(12) United States Patent
Ametaj

(10) Patent No.: US 9,415,062 B2
(45) Date of Patent: *Aug. 16, 2016

(54) USE OF BACTERIAL ENDOTOXINS AND LIPOTEICHOIC ACIDS TO IMPROVE POSTPARTAL HEALTH AND PRODUCTIVITY OF DAIRY COWS AND THEIR NEWBORNS

(76) Inventor: Burim N. Ametaj, Edmonton (CA)

( * ) Notice: Subject to any disclaimer, the term of this patent is extended or adjusted under 35 U.S.C. 154(b) by 24 days.

This patent is subject to a terminal disclaimer.

(21) Appl. No.: 14/002,244

(22) PCT Filed: Feb. 29, 2012

(86) PCT No.: PCT/CA2012/050120
§ 371 (c)(1),
(2), (4) Date: Nov. 1, 2013

(87) PCT Pub. No.: WO2012/116447
PCT Pub. Date: Sep. 7, 2012

(65) Prior Publication Data
US 2014/0323430 A1  Oct. 30, 2014

Related U.S. Application Data

(60) Provisional application No. 61/448,815, filed on Mar. 3, 2011.

(51) Int. Cl.
*A61K 31/739* (2006.01)
*A61K 31/715* (2006.01)
*A61K 38/16* (2006.01)

(52) U.S. Cl.
CPC ............. *A61K 31/739* (2013.01); *A61K 31/715* (2013.01); *A61K 38/164* (2013.01)

(58) Field of Classification Search
CPC . A61K 38/164; A61K 31/715; A61K 31/719; A61K 2300/00
USPC .......................................................... 514/54
See application file for complete search history.

(56) References Cited

U.S. PATENT DOCUMENTS

| 4,141,970 A * | 2/1979 | Chidlow et al. ............ 424/282.1 |
| 2002/0051793 A1* | 5/2002 | Drabick .................... 424/236.1 |
| 2004/0147010 A1 | 7/2004 | Vidal et al. |
| 2006/0153869 A1* | 7/2006 | MacAdam ................. 424/203.1 |

OTHER PUBLICATIONS

Souba, W.W. et al, Ann. Surg., May 1990, pp. 543-549.*
Barshop, B.A., Encyclopedia.com, 2003, pp. 1-5.*
International Search Report for related PCT Patent Application No. PCT/CA2012/050120 dated Jun. 5, 2012.
Lehner, M.D. et al. "Induction of cross-tolerance by lipopolysaccharide and highly purified lipoteichoic acid via different toll-like receptors independent of paracrine mediators", The Journal of Immunology (2001), 166:5161-5167.
Kim, H.G. et al. "Lipoteichoic acid isolated from Lactobacillus plantarun inhibits lipopolysaccharide-induced TNF-α production in THP-1 cells and endotoxin shock in mice", The Journal of Immunology (2008), 180:2553-2561.

* cited by examiner

*Primary Examiner* — Ganapathy Krishnan
(74) *Attorney, Agent, or Firm* — Husch Blackwell LLP

(57) ABSTRACT

A combination of a bacterial endotoxin, in particular a lipopolysaccharide, and a lipoteichoic acid for treating or preventing a metabolic disorder or bacterial infection, or for improving milk energy efficiency in a subject. The combination may be administered separately, simultaneously or sequentially to a subject.

8 Claims, 38 Drawing Sheets

USE OF BACTERIAL ENDOTOXINS AND LIPOTEICHOIC ACIDS TO IMPROVE POSTPARTAL HEALTH AND PRODUCTIVITY OF DAIRY COWS AND THEIR NEWBORNS

CROSS REFERENCE TO RELATED APPLICATIONS

This application claims the benefit of and priority from U.S. Provisional Patent Application No. 61/448,815 filed Mar. 3, 2011, which is incorporated herein by reference in its entirety.

FIELD OF THE INVENTION

The invention concerns the use of bacterial endotoxins and lipoteichoic acids to improve postpartal health and productivity of dairy cows and their newborns.

BACKGROUND

The transition period is critical for the health and productivity of dairy cows due to high incidence of metabolic disorders caused by various bacterial infections. Metabolic disorders are diseases that involve changes in plasma metabolites of sick animals or humans. Almost 50% of dairy cows are affected by one or more metabolic diseases such as ketosis, fatty liver, laminitis, displaced abomasum, milk fever, downer cow syndrome, udder edema, metritis, retained placenta, infertility, or mastitis. The conventional view on metabolic disorders is that these diseases are related to the disturbance of one or more blood metabolites. These changes are generally interpreted as deficiencies or excesses of these nutrients in the diet, especially, around parturition.

High-grain diets (i.e. a diet rich in starch) may be implicated in the development of metabolic disorders. Feeding ruminant animals high-grain diets is a human designed intervention to increase milk and meat production. However, ruminants do not naturally consume high-grain diets; rather, they eat mostly grass or forage diets. Since grain is rich in starch and poor in fiber content, feeding high-grain diets is associated with major changes in the gastrointestinal (GI) microflora switching from fiber-digesting bacteria into starch-digesting bacteria. Most of the starch-digesting bacteria are Gram-negative bacteria. The latter degrade starch to use it for their nutritional needs. During this process large quantities of acids are released into the GI tract, changing the pH from normally alkaline into acidic pH. Furthermore, abundant starch increases the number of Gram-negative bacteria in the GI tract. This is associated with the release of great amounts (20-fold increase) of toxic compounds such as endotoxin or lipopolysaccharide (LPS). Endotoxin translocates into the host's blood circulation and causes a variety of alterations in blood metabolites, immunity, and health status.

Research work indicates that lipoteichoic acid (LTA) is able to induce an inflammatory response and dysfunction of multiple organs, know as septic shock, when administered intravenously (iv) in experimental animals. An early investigation demonstrated that iv infusion of LTA was associated with the release of tumor necrosis factor alpha and interferon gamma in the plasma, a decrease in the arterial oxygen pressure in the lungs, and increases in the plasma concentrations of bilirubin, alanine aminotransferase, creatinine and urea, lipase from pancreas, and creatine kinase. In addition, LTA causes the release of nitric oxide in multiple organs, circulatory failure, and 50% mortality in the experimental animals (De Kimpe S. J. et al., 1995). Moreover, research from different groups has shown that even a single dose of LTA, as little as 0.1 mg, is sufficient to produce enhanced concentrations of free fatty acids (FFA) and triglyceride in the blood of experimental animals. Lipoteichoic acid also has been shown to increase the concentration of cholesterol in the plasma. Additionally, mounting evidence indicates involvement of LTA in the pathogenesis of mastitis in dairy cows. Thus, recent work demonstrated that that infusion of LTA alone in the mammary gland was sufficient to elicit a marked inflammatory response in the mammary gland of dairy cows, characterized by a massive influx of neutrophils into milk. This suggests that during infection, LTA contributes to the recruitment of neutrophils There remains a need for effective combinations and methods to improve postpartal health and productivity of dairy cows and their newborns.

SUMMARY

In one aspect, the invention provides a combination comprising a bacterial endotoxin and a lipoteichoic acid. In an embodiment, the combination is for separate, simultaneous or sequential administration to a subject for treating or preventing a metabolic disorder, for treating or preventing bacterial infection or for improving milk energy efficiency in said subject.

In another aspect, the invention provides a method for treating or preventing a metabolic disorder, for treating or preventing bacterial infection or for improving milk energy efficiency in a subject, said method comprising administering to said subject a bacterial endotoxin and a lipoteichoic acid, separately, simultaneously or sequentially.

DETAILED DESCRIPTION

Figure 1:
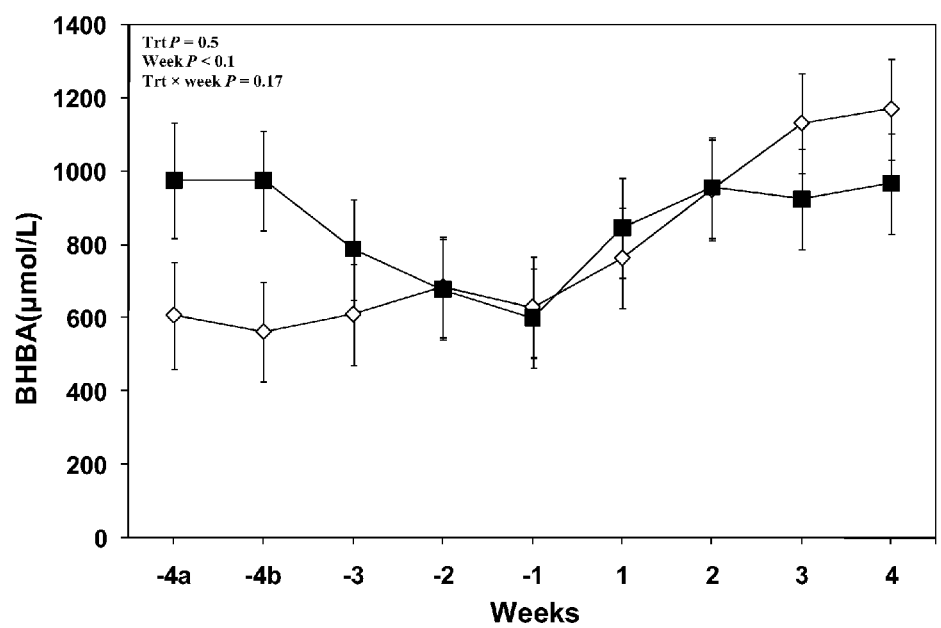
FIG. 1 is a graph depicting weekly variations of overall beta-hydroxybutyrate in plasma of multiparous and primiparous Holstein cows challenged with oral and nasal treatment of LPS-LTA (TRT; ■) or saline (CTR; ◊) (LSM±SEM; n=16; Trt=effect of treatment; Week=effect of sampling week, Trt×Week=effect of treatment by sampling week).

Metabolic disorders are a group of diseases that affect dairy cows immediately after parturition. There are several metabolic disorders identified in dairy cows during the first month after parturition, the most significant of which are the following: (1) sub-acute and acute ruminal acidosis; (2) laminitis; (3) ketosis, (4) fatty liver, (5) left displaced abomasum (LDA), (6) milk fever; (7) downer cow; (8) retained placenta; (9) metritis, (10) mastitis, (11) udder edema; and (12) bloat. Dairy farmers lose approximately $142/cow per year for treatment of metabolic disorder in addition to milk loss in the first 30 days of lactation. More than half of dairy cows are affected by at least one metabolic disorder. This makes metabolic disorders of great economic importance.

The reason that these diseases are called metabolic disorders is related to the fact that they are associated with the disturbance of one or more blood metabolites in sick cows. For example, ketosis is associated with enhanced ketone bodies in the blood; fatty liver is associated with enhanced non-esterified fatty acids (NEFA) in the blood and their accumulation in the liver; acidosis is associated with increased production of volatile fatty acid (i.e., acetate, propionate, and butyrate) and organic acids (e.g., lactic acid) in the rumen and low rumen and blood pH; and milk fever is associated with decreased blood calcium. There is not yet a blood metabolite identified for some of the metabolic disorders such as downer cow, LDA, metritis, mastitis, or bloat. However, these diseases are associated with alteration of multiple blood metabolites.

The most interesting observation with regards to the occurrence of metabolic disorders is that they are highly associated with each other. For example, cows affected by milk fever are more prone to mastitis, retained placenta, metritis, LDA, dystocia, udder edema, and ketosis; cows affected by acidosis are more prone to laminitis, LDA, milk fever, mastitis, and fatty liver. Those affected by retained placenta are more prone to metritis, LDA, and ketosis. Ketosis and fatty liver are common findings in cows affected by milk fever, mastitis, laminitis, displaced abomasum, metritis, retained placenta and udder edema. Although these associations have been known for years by animal scientists, the reason behind this association is not very well understood. One speculation is that there might be a common etiological factor that initiates the cascade of metabolic disorders. Therefore, scientists are searching to identify such a common causal agent of metabolic disorders; however, no such an agent has been identified so far.

Modern dairy cows have been selected by continuous genetic improvement and rigorous selection to achieve high milk production. Since high milk production cannot be maintained by forage alone grain-based diets which are very rich in energy are fed to the cows. The ruminal digestive system is not developed to digest high amounts of grain and feeding grains which are rich in starch is associated with a decline in ruminal and colonic pH, change in osmotic pressure and shift in bacterial populations from cellulolytic to amylolytic bacteria. Most of the known starch digesters are Gram-negative bacteria and this shift in population is associated with a 20-fold increase in the amount of endotoxin in the ruminal fluid. Several epidemiological studies have shown that endotoxin from rumen Gram-negative bacteria has been implicated in diseases that are related to feeding high concentrate diets such as sudden death syndrome, ruminal acidosis, fatty liver, left displaced abomasum and laminitis. Ruminal epithelium lacks in mucus secretion and exposure to acidotic environment leads to inflammation and tissue degeneration. The acidotic environment, change in osmotic pressure and endotoxin may affect the permeability of the rumen and colon resulting in translocation of endotoxin in the circulation. Although the presence of endotoxin in the ruminal fluid has been documented, prior to the present invention there has been no convincing evidence of translocation into the circulation.

The main objective of this investigation was to apply repeated oral administration of lipopolysaccharide (LPS) a cell wall component of Gram-negative (GN) bacteria and lipoteichoic acid (LTA) a cell wall component of Gram-positive (GP) bacteria around parturition to prevent metabolic disturbances induced by those compounds and development of inflammatory states related to both GN and GP bacteria as well as improve general health, and productivity of dairy cows.

Pregnant Holstein dairy cows were blocked by parity and the anticipated day of calving, and were randomly allocated to 2 groups, 28 d before the expected day of parturition. Cows were orally administered saline solution (Control group), or saline solution containing 3 increasing doses of LPS (Treatment group) form *Escherichia coli* 0111:B4 along with a LTA from *Bacillus subtilis* with the same dose pre-partum. The dose of LTA was determined from a preliminary dosage study. Blood, urine, saliva, and vaginal mucus samples were collected 4 weeks before and 4 weeks after calving, whereas milk samples were collected starting from calving until 4 weeks after calving for all cows in the experiment to be analyzed for different variables. Cows were observed daily for presence of clinical disease during the 4 weeks before and 4 weeks after calving and rectal temperatures were taken during 3 weeks before and 2 weeks after calving. Blood samples were also obtained from the newborns during the 4 weeks after birth in order to measure the immunity transmitted to the newborn calves from the dam. Calves were also observed for incidence of diarrhea until 4 weeks after birth.

To investigate the diurnal blood and health responses in treated cows, blood and health records were taken at −15 min before as well as 1, 3 and 5 h after application of the oral vaccine. Results of this study demonstrated that oral administration of LPS and LTA was associated with lower incidence of metritis, laminitis, retained placenta, and improved uterine horn fluctuation in the treated cows. Furthermore, the severity of laminitis was lowered in treated multiparous cows, where it tended to be lower in the treatment group. Moreover, treated cows tended to require lower overall number of medications as well as have lower number of days with more than one disease versus control cows. Blood data showed lower plasma lactate in treated cows and a tendency for higher plasma cholesterol, which is an indication of better energy status in those cows.

Treatment did not influence plasma BHBA, NEFA, and glucose. Interestingly, data indicated that the oral vaccination of cows with LPS and LTA increased their milk energy efficiency, which was associated with a trend for greater feed intake in that group. Furthermore, the analysis of milk data demonstrated a higher fat to protein ratio, as well as greater milk fat efficiency for the treated cows. No effect of treatment was observed on other milk components as well as on the overall milk production. Calf data indicated a tendency for lower calf diarrhoea score in the treatment group for both multiparous and primiparous cows compared to controls.

Overall, administration of oral LPS and LTA improved metabolic and productive performance as well as general health status of the treated cows suggesting application of this novel vaccine during the transition period is a very promising intervention to improve general health, productivity, and wellbeing of dairy cows and the newborns.

Endotoxin

Any bacterial endotoxin may be used in the practice of the invention. Endotoxins are cell-associated bacterial toxins. They generally compose part of the outer membrane of the cell wall of Gram-negative bacteria, whether pathogenic or not, such as *Escherichia coli, Salmonella, Shigella, Pseudomonas, Neisseria,* or *Haemophilus*. Many endotoxins are lipopolysaccharides (LPS), comprising a lipid component and a polysaccharide component. Toxicity of the endotoxin is associated with the lipid component (lipid A) and immunogenicity is associated with the polysaccharide component. Both lipid A and the polysaccharide components of LPS act as determinants of virulence in Gram-negative bacteria.

The structure of the lipid A component is highly conserved amongst Gram-negative bacteria. The polysaccharide component contains two regions. The first is known as the core (R) antigen or (R) polysaccharide. The core polysaccharide remains relatively constant within a bacterial genus but is structurally distinct amongst genera of bacteria. The second polysaccharide region is the somatic (O) antigen or (O) polysaccharide. The (O) polysaccharide varies substantially between species and even amongst strains of Gram-negative bacteria.

Endotoxins of the invention may be used in purified or unpurified form. For example, in certain applications, it may be sufficient to provide the endotoxin in the form of killed bacteria, such as lysed bacteria or even as live bacteria. In other applications, purified endotoxins (for instance in crystalline form) may be used and are available from commercial sources such as Sigma-Aldrich. Synthetic endotoxins, such as synthetic LPS or LPS analogs may be used in practice of the invention. Truncated endotoxins, or portions or fractions of endotoxins comprising only the lipid A or core polysaccharide or (O) polysaccharide of LPS may be used as may be chimeric endotoxins comprising an altered or heterologous lipid A or polysaccharide components.

Lipoteichoic Acid

Any lipoteichoic acid may be used in the practice of the invention. Lipoteichoic acids are a major constituent of the cell wall of Gram-positive bacteria such as *Bacillus subtilis*. Lipoteichoic acids consist of teichoic acids, long-chain ribitol phosphate and glyceride lipid membrane anchor. One function of lipoteichoic acids is as regulators of autolytic cell wall enzymes called muramidases. Lipoteichoic acids also have potent antigenic properties and can stimulate an immune response when released from bacterial cells, for instance, after bacteriolysis induced by lysozyme, cationic peptides from leucocytes, or beta-lactam antibiotics.

Lipoteichoic acids of the invention may be used in purified or unpurified form. For example, in certain applications, it may be sufficient to provide the lipoteichoic acid in the form of killed bacteria, such as lysed bacteria or even as live bacteria. In other applications, purified lipoteichoic acids (for instance in crystalline form) may be used and are available from commercial sources such as Sigma-Aldrich. Synthetic lipoteichoic acid, such as synthetic LTA or LTA analogs may be used in practice of the invention. Truncated lipoteichoic acids, or portions or fractions of lipoteichoic acids may be used as may be chimeric lipoteichoic acids comprising an altered or heterologous teichoic acids, ribitol phosphate chains glyceride components.

Combinations and Compositions

The endotoxin and lipoteichoic acid may be administered to a subject in the form of, without limitation, a combination comprising a bacterial endotoxin and a lipoteichoic acid, said combination being for separate, simultaneous or sequential administration. The combinations may comprise one or more pharmaceutical compositions. Pharmaceutical compositions may be for mucosal, oral, nasal, rectal, intravaginal or other modes of administration. The composition comprises the endotoxin and/or the lipoteichoic acid in combination with one or more physiologically acceptable ingredients, such as carriers, excipients and/or diluents. Compositions and formulations for oral administration are particularly preferred.

Pharmaceutical compositions may be prepared, for example, in unit dose forms, such as tablets, sachets, capsules, dragees, suppositories or ampoules. They may be prepared in a conventional manner, for example by means of conventional mixing, granulating, confectioning, dissolving or lyophilising processes.

Preferred are pharmaceutical compositions formulated for administration to the gastrointestinal tract, such as by oral or rectal administration. Oral administration is particularly preferred as a convenient and economical mode of administration. Pharmaceutical compositions of the present invention in the form of dosage units for oral administration may take the form of, for example, granules, tablets, capsules, liquids or dragees prepared together with physiologically acceptable carriers, excipients and/or diluents. Pharmaceutical compositions of the present invention may be applied to or incorporated into, for example, animal feed, fodder, silage, foodstuffs and drinking water.

Typical physiologically acceptable ingredients include:
(a) binding agents such as starch (e.g. pregelatinised maize starch, wheat starch paste, rice starch paste, potato starch paste), polyvinylpyrrolidone, hydroxypropyl methylcellulose, gum tragacanth and/or gelatin;
(b) fillers such as sugars (e.g. lactose, saccharose, mannitol, sorbitol), amylopectin, cellulose preparations (e.g. microcrystalline cellulose), calcium phosphates (e.g. tricalcium phosphate, calcium hydrogen phosphatelactose) and/or titanium dioxide;
(c) lubricants such as stearic acid, calcium stearate, magnesium stearate, talc, silica, silicic acid, polyethylene glycol and/or waxes;
(d) disintegrants such as the above-mentioned starches, carboxymethyl starch, cross-linked polyvinylpyrrolidone, agar, alginic acid or a salt thereof (e.g. sodium alginate) and/or sodium starch glycollate;
(e) wetting agents such as sodium lauryl sulphate; and/or,
(f) stabilizers.

Soft gelatin capsules may be prepared with capsules containing a mixture of the bacterial endotoxin and/or lipoteichoic acid together with paraffin oil, liquid polyethylene glycols, vegetable oil, fat and/or another suitable vehicle for soft gelatin capsules. Plasticizers such as glycerol or sorbitol may also be used. Hard gelatin capsules may contain granules of the composition. Hard gelatin capsules may also contain the endotoxin and/or lipoteichoic acid in combination with solid powdered ingredients such as those listed above.

Liquid formulations for oral administration may be prepared in the form of solutions, syrups or suspensions. Liquid formulations typically comprise the bacterial endotoxin and/or the lipoteichoic acid together with an excipient such as sugar or sugar alcohols, and a carrier such as ethanol, water, glycerol, propylene glycol, polyethylene glycol, almond oil, oily esters or mixtures thereof. If desired, such liquid formulations may also contain coloring agents, flavoring agents, saccharine, thickening agents (e.g. carboxymethyl cellulose), suspending agents (e.g. sorbitol syrup, methyl cellulose, hydrogenated edible fats), emulsifying agents (e.g. lecithin, acacia), and/or preservatives (e.g. methyl p-hydroxybenzoates, propyl p-hydroxybenzoates, sorbic acid). Liquid formulations for oral administration may also be prepared in the form of a dry powder to be reconstituted with water or another suitable vehicle prior to use.

The invention also provides kits or commercial packages comprising a composition as described above together with printed matter comprising instructions for using the composition for treating or preventing a metabolic disorder, for treating or preventing bacterial infection or for improving milk energy efficiency in a subject.

The pharmaceutical composition will generally contain a therapeutically effective amount of the bacterial endotoxin and/or the lipoteichoic acid, i.e. an amount that is effective, at dosages and for periods of time necessary, to achieve a desired prophylactic or therapeutic result, such as a reduction, inhibition, or prevention of disease onset or progression. A therapeutically effective amount may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

For any particular subject, specific dosage regimens may be adjusted over time according to the individual need and the professional judgement of the person administering or supervising the administration of the compositions.

In some embodiments wherein the subject is a pregnant animal such as a dairy cow, the composition is administered to the subject from a time no more than four weeks prior to parturition to a time no more than four weeks after parturition. During this period the composition may preferably be administered about two times per week. The composition may be administered in a dose of from 0.01 to 1 µg endotoxin/kg body weight of the subject, more preferably from 0.01 to 0.05 µg endotoxin/kg body weight of the subject, even more preferably at a dose of about 0.01, about 0.05 or about 0.1 µg endotoxin/kg body weight of the subject.

In other embodiments, the composition may be administered in a dose comprising from 0.1 to 1000 µg lipoteichoic acid, more preferably from 1 to 500 µg lipoteichoic acid, more preferably from 100 to 250 µg lipoteichoic acid, and even more preferably about 100, about 120 or about 250 µg lipoteichoic acid.

Subjects

Compositions of the invention may be used in prevention of metabolic disorders in a wide range of subjects including mammals and birds, including, without limitation: humans; livestock such as cattle, horses, goats, sheep, and pigs; companion animals such as dogs and cats; and domesticated fowl such as chickens, ducks and geese.

In one embodiment, the subject is a ruminant mammal, such as, without limitation, a cow, goat, sheep, llama, bison or deer. In an embodiment, the subject is a pregnant or has recently given birth, such as a ruminant mammal within about 4 weeks before or after parturition.

Disorders

The compositions of the invention are useful for treating or preventing metabolic disorders and bacterial infections. As used herein, "treating or preventing" is intended to encompass curing as well as ameliorating at least one symptom of the metabolic disorder or bacterial infection, as well as obtaining beneficial or desired results including and preferably clinical results, delaying the development or progression of or decreasing symptoms of a metabolic disorder or bacterial infection, increasing the quality of life of those suffering from the metabolic disorder or bacterial infection, decreasing the dose of other medications required to treat the metabolic disorder or bacterial infection, prolonging survival of a subject suffering from the metabolic disorder or bacterial infection, causing the clinical symptoms of the metabolic disorder or bacterial infection not to develop by administration of a protective composition prior to the induction of clinical symptoms, and/or preventing recurrence of the metabolic disorder or bacterial infection.

A metabolic disorder may be caused by or associated with parturition in the subject and/or the feeding of a diet containing an elevated proportion of grain-based feed or easily digestible carbohydrates. The metabolic disorder may be associated with or caused by increased permeability of the colon or rumen, particularly increased permeability that permits bacterial endotoxins or lipoteichoic acids to escape the rumen or colon and infiltrate the bloodstream. Metabolic disorders that may be treated or prevented in animals, particularly ruminant mammals include without limitation ruminal acidosis, laminitis, ketosis, fatty liver, left displaced abomasum, milk fever, downer cow, retained placenta, metritis, mastitis, udder edema or bloat. Metabolic disorders that may be treated or prevented in humans include, without limitation abdominal obesity, impaired glucose regulation, raised triglycerides, decreased high-density lipoprotein cholesterol, elevated blood pressure, hyperinsulinemia with underlying insulin resistance, atherosclerosis, cardiovascular disease or rheumatic inflammatory disease.

Bacterial infections that may be treated or prevented include, without limitation, bacterial infections caused by endotoxin-producing Gram-negative bacteria, including, without limitation *Escherichia coli, Salmonella, Shigella, Pseudomonas, Neisseria,* or *Haemophilus* or by lipoteichoic acid-producing Gram-positive bacteria, including, without limitation *Bacillus subtilis, Staphylococcus, Streptococcus,* or *Enterococcus.*

Improving Milk Energy Efficiency

The compositions of the invention are also useful for improving milk energy efficiency in a subject. In one embodiment, improvement of milk energy efficiency comprises increased fat to protein ratio. In other embodiments, improvement of milk energy efficiency comprises increased milk fat efficiency. As used herein, "milk energy efficiency" (MEE) is intended to encompass the amount of milk fat in grams per kilogram of dry matter intake, and may be calculated with the following formula:

MEE(Mcal/kg milk)=0.0929*% fat+0.0547*% Crude Protein+0.0359*% lactose.

The invention is further illustrated by the following non-limiting examples.

EXAMPLE 1

In an experiment conducted at Dairy Research and Technology Centre (DRTC; University of Alberta), thirty primiparous and multiparous Holstein dairy cows were selected for this experiment from the Dairy Research and Technology Centre (DRTC), University of Alberta.

Materials and Methods

Half of the cows were treated orally with lipopolysaccharide (LPS) from *Escherichia coli* 0111:B4 and lipoteichoic acid (LTA) from *Bacillus subtilis* to prevent development of periparturient diseases related to LPS and LTA. At approximately 28 d before the expected day of calving thirty pregnant primiparous and multiiparous cows were equally assigned into two groups (n=15 per each group) including subgroups of n=10 cows and n=5 heifers for post vaccination sampling. Based on their parity, body condition score, and milk production from previous year cows were assigned to one of the two groups.

Cows n=15 per each group) were orally administered either 2 mL of saline solution (Control group), or 2 mL of saline solution containing LPS from *E. coli* strain 0111:B4 at three increasing concentrations as follows: 1) 0.01 μg/kg BW on d −28 and −24, 2) 0.05 μg/kg BW on d −21 and −18, and 0.1 μg/kg BW on d −14 along with a flat dose of LTA from *Bacillus subtilis* (i.e. 120 μg/animal) twice per week for 3 consecutive weeks starting from 4 wk pre-partum (Treatment group). The initial crystalline *Escherichia coli* LPS (Lipopolysaccharide-FITC from *E. coli* strain 0111:B4 purchased from Sigma-Aldrich Canada Ltd.) containing 10 mg of purified LPS was dissolved in 10 mL of distilled water as suggested by the manufacturer and stored a refrigerator at +4° C. For administration to the animal the daily dose was dissolved in 2 mL of saline and then introduced into the oral cavity of the cows using 5 mL disposable syringes. Similarly, the same amount of carrier (i.e., 2 mL saline) was orally sprayed to all cows in the control group.

All experimental procedures were approved by the University of Alberta Animal Care and Use Committee for Livestock, and animals were cared for in accordance with the guidelines of the Canadian Council on Animal Care (1993). Veterinary supervision was provided to the animals throughout the experiment.

Sampling and Analyses

Blood, saliva, vaginal mucus, and milk samples were collected twice per week on day 1 and 3 of wk −4, −3, and −2 before the expected day of calving. All samples were collected before the administration of vaccine. Blood samples from both the daily and post vaccination sampling were analyzed for the following metabolites: beta-hydroxybutiric acid (BHBA; Wako Chemicals, Inc., Richmond, Va., USA), cholesterol (Diagnostics Chemicals Ltd., Charlottetown, PE, Canada), cortisol (Diagnostic Chemicals Ltd., Charlottetown, PE, Canada), glucose (Diagnostic Chemicals Ltd., Charlottetown, PE, Canada), non-esterified fatty acids (NEFA; Wako Chemicals, USA, Inc., Richmond, Va.), and insulin (Mercodia Inc., Winston Salem, N.C., USA). Additionally, acute phase proteins (APP) including haptoglobin (Hp; Tridelta Diagnostics Ltd, Morris Plains, N.J., USA; finished) were analyzed, whereas two more APP including C-reactive protein (ALPCO Diagnostics Ltd., Morris Plains, N.J., USA), and lipopolysaccharide-binding protein (HBT, Canton, Mass., USA) will be analyzed in the near future. Plasma is analyzed for anti-LPS antibodies including immunoglobulin A (IgA), IgG, and IgM (HBT Endocab test kit HK504, Canton, Mass., USA). Plasma and milk samples are tested for content of endotoxin by the chromogenic LAL test (CapeCode Inc., MA, USA) and for LTA. Milk samples were also analyzed for fat, protein, lactose, somatic cell counts (SCC), and milk urea nitrogen (MUN) at CanWest, Dairy Herd Improvement laboratory (DHI), Edmonton, Alberta, Canada.

All treated cows were observed clinically for up to 6 h after vaccination by measuring their rectal temperature, rumen contraction rate, and respiration rate. A dose study was conducted to determine the dose of LPS to be used for oral treatment without causing clinical symptoms to the animals. Blood samples from dose study were collected several hours after oral treatment with LTA. Those samples were also analyzed for various plasma metabolites. Disease incidence, dry matter intake (DMI), body condition score (BCS), manure score, and milk production records were collected for all dairy cows during 4 wk before and 4 wk after parturition. Reproduction records were followed until conception or until a cull decision was taken.

Statistics

Data were analyzed using the MIXED procedure of SAS (SAS Institute Inc., Cary, N.C., USA Version 9.1.3) as describe by the following model:

$$Y_{ijkl} = m + t_i + w_j + tw_{ij} + e_{ijkl}$$

where $Y_{ijkl}$ is the observations for the dependent variables, m represent the population mean, $t_i$ is the fixed effect of treatment, $w_j$ is the fixed effect of week, $tw_{ij}$ is the interaction between treatment and week, and $e_{ijkl}$ is the residual error assumed to be normally distributed. The PDIFF option of SAS was used to compare the LSM. Measurements on the same animal were considered as repeated measures. The covariance structure of the repeated measurements for each variable was modeled separately according to the lowest values of fit statistics based on the BIC (Bayesian information criteria). The significance limit was declared at P<0.05.

EXAMPLE 2

The main objective of this investigation was to apply repeated oral administration of lipopolysaccharide (LPS) a cell wall component of Gram-negative (GN) bacteria and lipoteichoic acid (LTA) a cell wall component of Gram-positive (GP) bacteria around parturition to prevent metabolic disturbances induced by those compounds and development of inflammatory states related to both GN and GP bacteria as well as improve general health, and productivity of dairy cows.

Thirty pregnant Holstein dairy cows were blocked by parity and the anticipated day of calving, and were randomly allocated to 2 groups (n=15 cows per group), 28 d before the expected day of parturition. Cows were orally administered 2 mL of saline solution (Control group), or 2 mL of saline solution containing 3 increasing doses of LPS (Treatment group) form *Escherichia coli* 0111:B4 as follows: 1) 0.01 μg/kg BW on d −28 and −24, 2) 0.05 μg/kg BW on d −21 and −18, and 0.1 μg/kg BW on d −14 along with a LTA from *Bacillus subtilis* with the same dose (i.e. 120 μg/cow) prepartum. The dose of LTA was determined from a preliminary dosage study (see Example 3). Blood, urine, saliva, and vaginal mucus samples were collected 4 weeks before and 4 weeks after calving, whereas milk samples were collected starting from calving until 4 weeks after calving for all cows in the experiment to be analyzed for different variables.

Cows were observed daily for presence of clinical disease during the 4 weeks before and 4 weeks after calving and rectal temperatures were taken during 3 weeks before and 2 weeks after calving. Blood samples were also obtained from the newborns during the 4 weeks after birth in order to measure the immunity transmitted to the newborn calves from the dam. Calves were also observed for incidence of diarrhea until 4 weeks after birth. To investigate the diurnal blood and health responses in treated cows, blood and health records were taken at −15 min before as well as 1, 3 and 5 h after application of the oral vaccine.

Blood Metabolites Results

Figure 2:
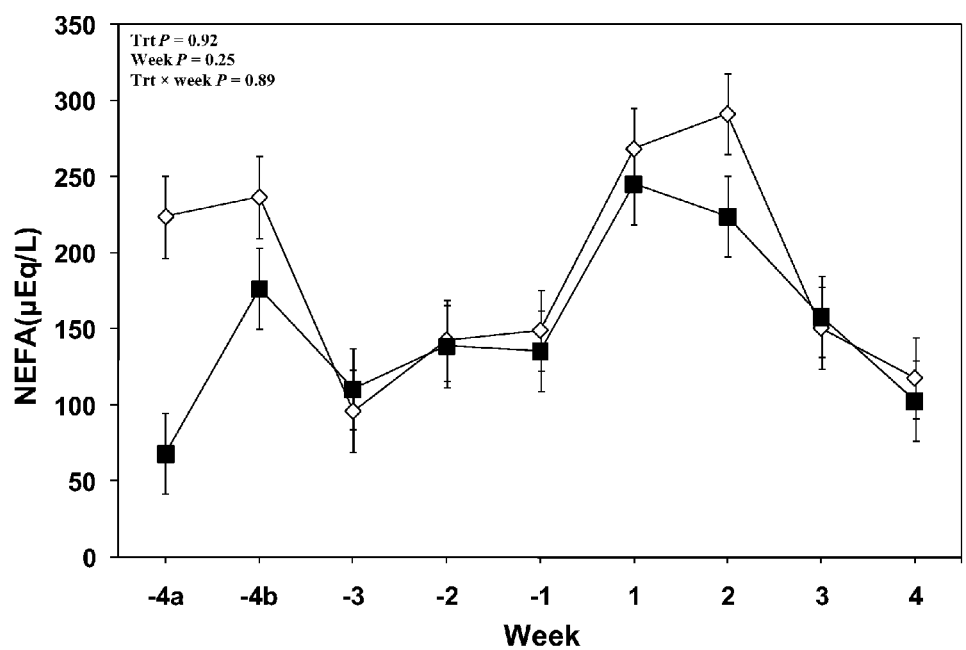
FIG. 2 is a graph depicting weekly variations of overall non-esterified fatty acids in plasma of multiparous and primiparous Holstein cows challenged with oral and nasal treatment of LPS-LTA (TRT; ■) or saline (CTR; ◊) (LSM±SEM; n=16; Trt=effect of treatment; Week=effect of sampling week, Trt×Week=effect of treatment by sampling week).
Figure 3:
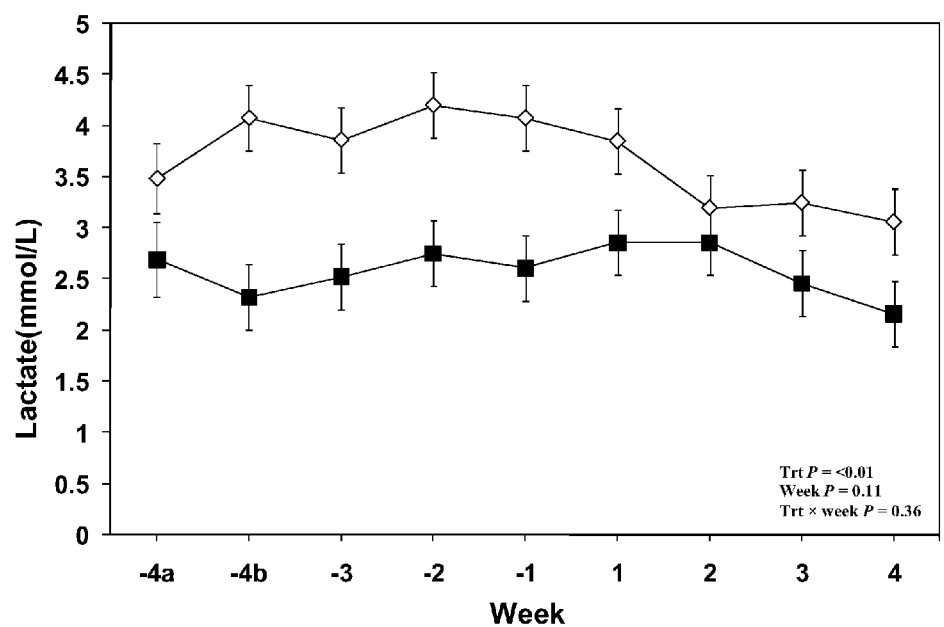
FIG. 3 is a graph depicting weekly variations of overall lactate in plasma of multiparous and primiparous Holstein cows challenged with oral and nasal treatment of LPS-LTA (TRT; ■) or saline (CTR; ◊) (LSM±SEM; n=16; Trt=effect of treatment; Week=effect of sampling week, Trt× Week=effect of treatment by sampling week).
Figure 4:
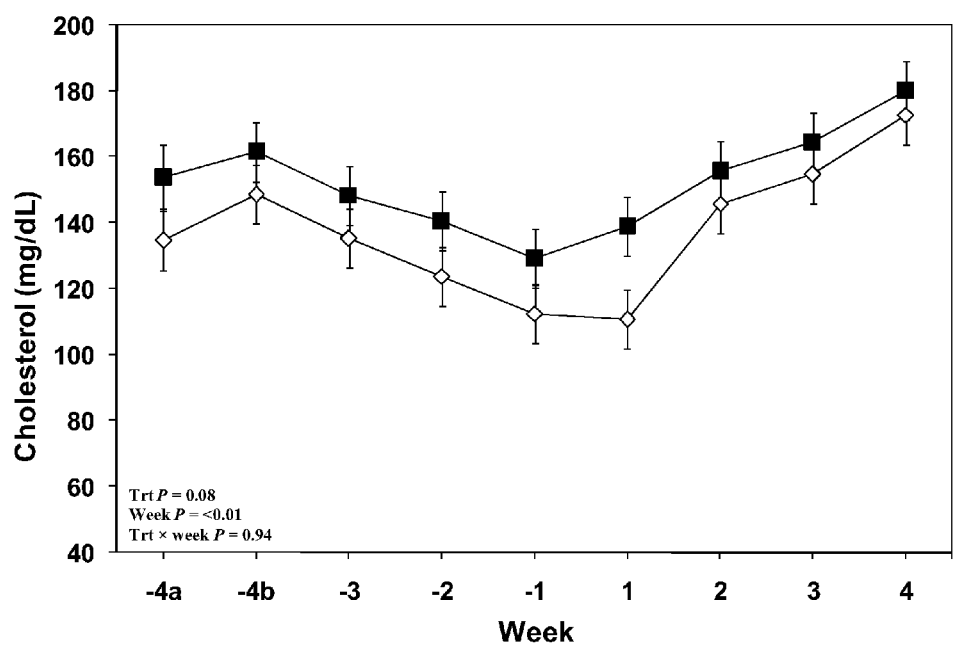
FIG. 4 is a graph depicting weekly variations of overall cholesterol in plasma of multiparous and primiparous Holstein cows challenged with oral and nasal treatment of LPS-LTA (TRT; ■) or saline (CTR; ◊) (LSM±SEM; n=16; Trt=effect of treatment; Week=effect of sampling week, Trt× Week=effect of treatment by sampling week).
Figure 5:
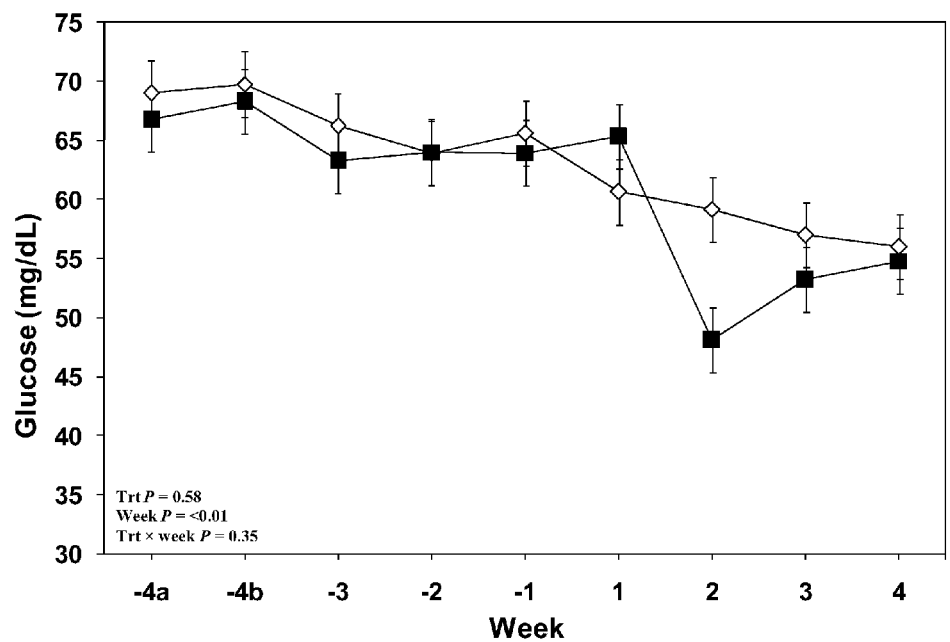
FIG. 5 is a graph depicting weekly variations of overall glucose in plasma of multiparous and primiparous Holstein cows challenged with oral and nasal treatment of LPS-LTA (TRT; ■) or saline (CTR; ◊) (LSM±SEM; n=16; Trt=effect of treatment; Week=effect of sampling week, Trt× Week=effect of treatment by sampling week).
Figure 6:
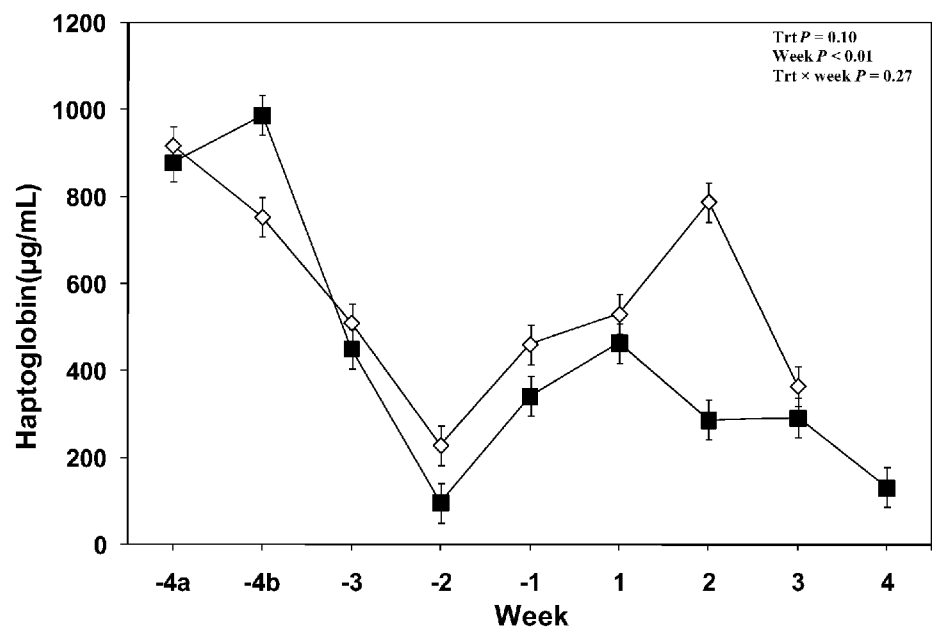
FIG. 6 is a graph depicting weekly variations of overall haptoglobin in plasma of multiparous and primiparous Holstein cows challenged with oral and nasal treatment of LPS-LTA (TRT; ■) or saline (CTR; ◊) (LSM±SEM; n=16; Trt=effect of treatment; Week=effect of sampling week, Trt×Week=effect of treatment by sampling week).

A indicated in FIG. 3, blood data showed lower plasma lactate in multiparous and primiparous Holstein cows challenged with oral and nasal treatment of LPS-LTA, as well as a tendency for higher plasma cholesterol (FIG. 4), which is an indication of better energy status in those cows. Treatment did not influence plasma BHBA, NEFA, or glucose (see FIGS. 1, 2 and 5).

Milk Composition Results

Figure 7:
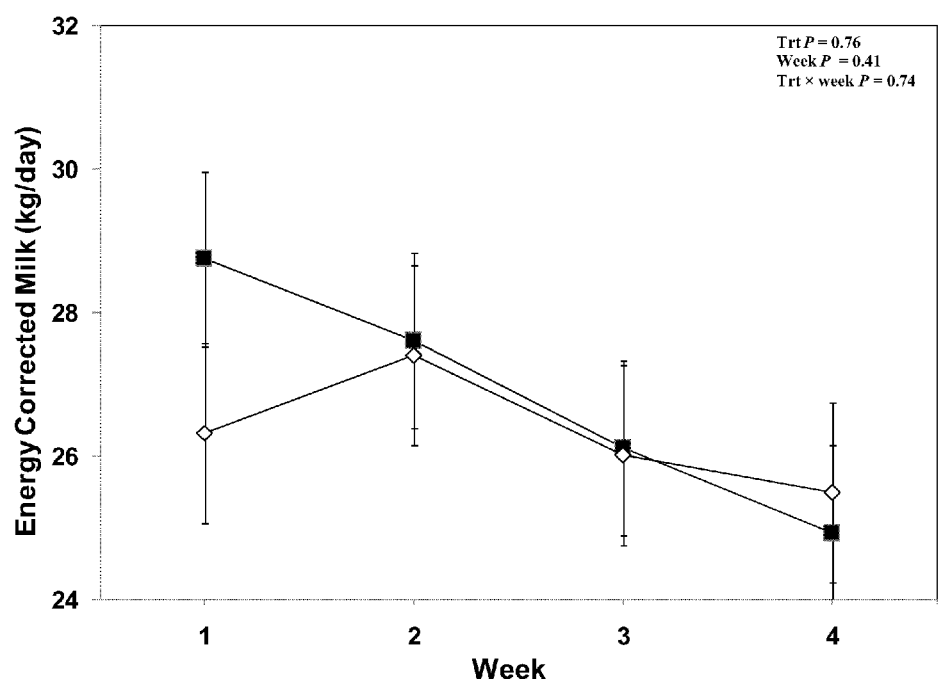
FIG. 7 is a graph depicting weekly variations of overall energy corrected milk in multiparous and primiparous lactating Holstein cows challenged with oral and nasal treatment of LPS-LTA (TRT; ■) or saline (CTR; ◊) (LSM±SEM; n=29; Trt=effect of treatment; Week=effect of sampling week, Trt×Week=effect of treatment by sampling week).
Figure 8:
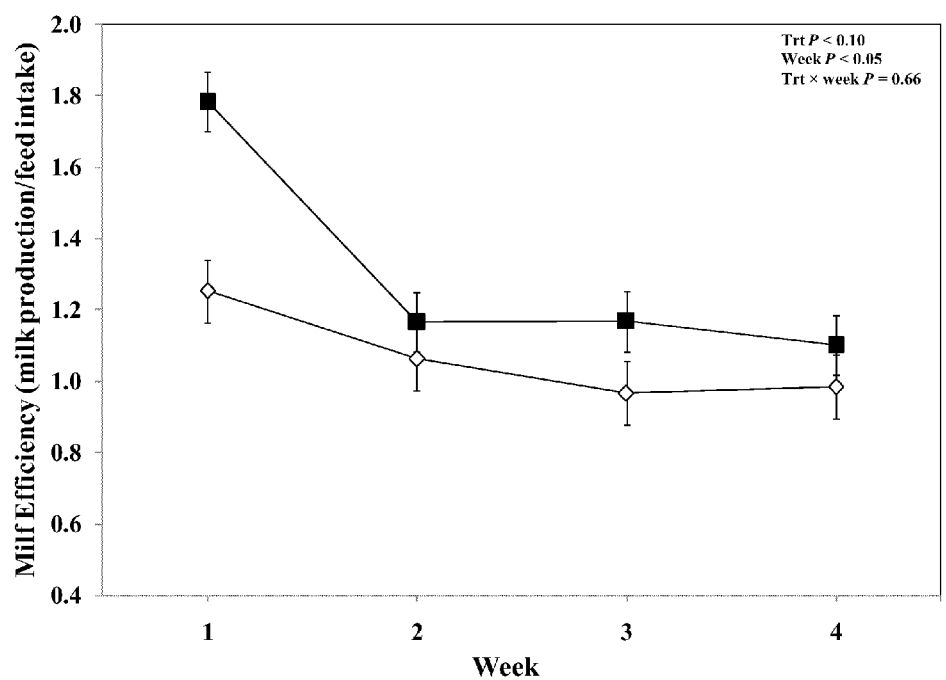
FIG. 8 is a graph depicting weekly variations of overall milk efficiency in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 13:
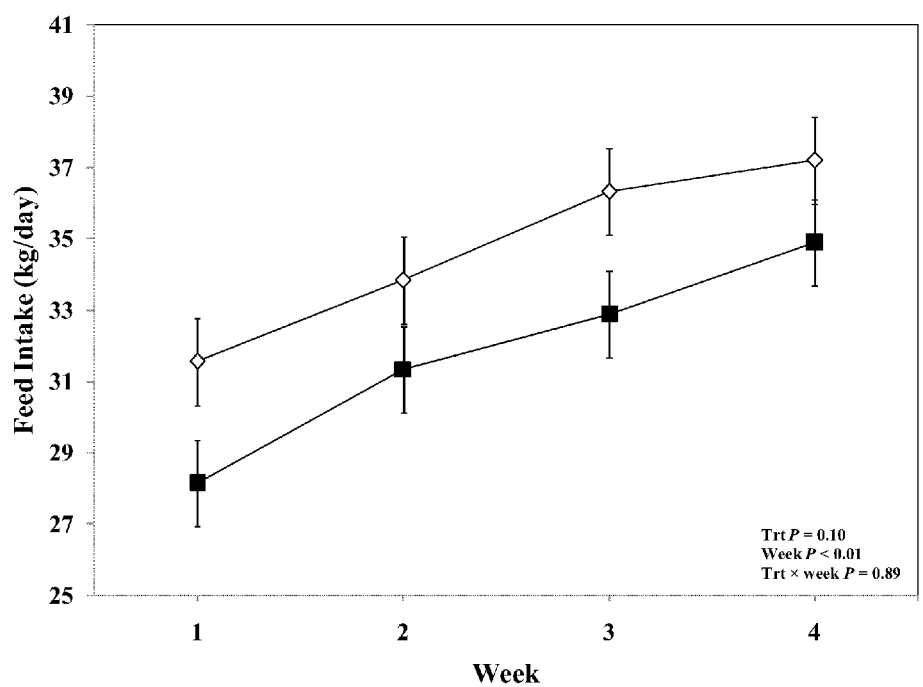
FIG. 13 is a graph depicting weekly variations of overall feed intake in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 14:
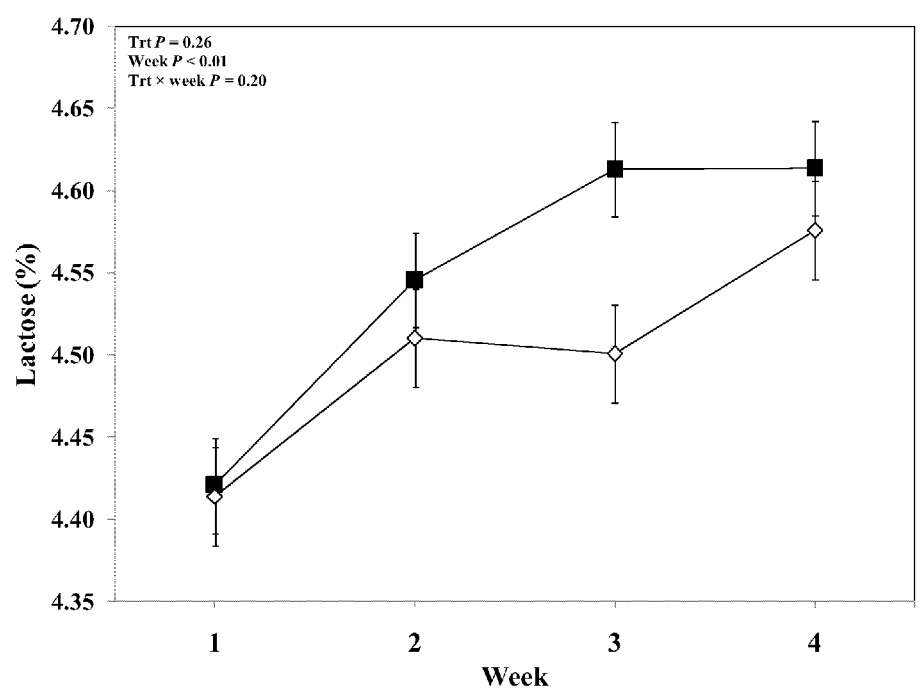
FIG. 14 is a graph depicting weekly variations of overall lactose content in multiparous and primiparous lactating Holstein cows challenged with oral and nasal treatment of LPS-LTA (TRT; ■) or saline (CTR; ◊) (LSM±SEM; n=29; Trt=effect of treatment; Week=effect of sampling week, Trt×Week=effect of treatment by sampling week).
Figure 15:
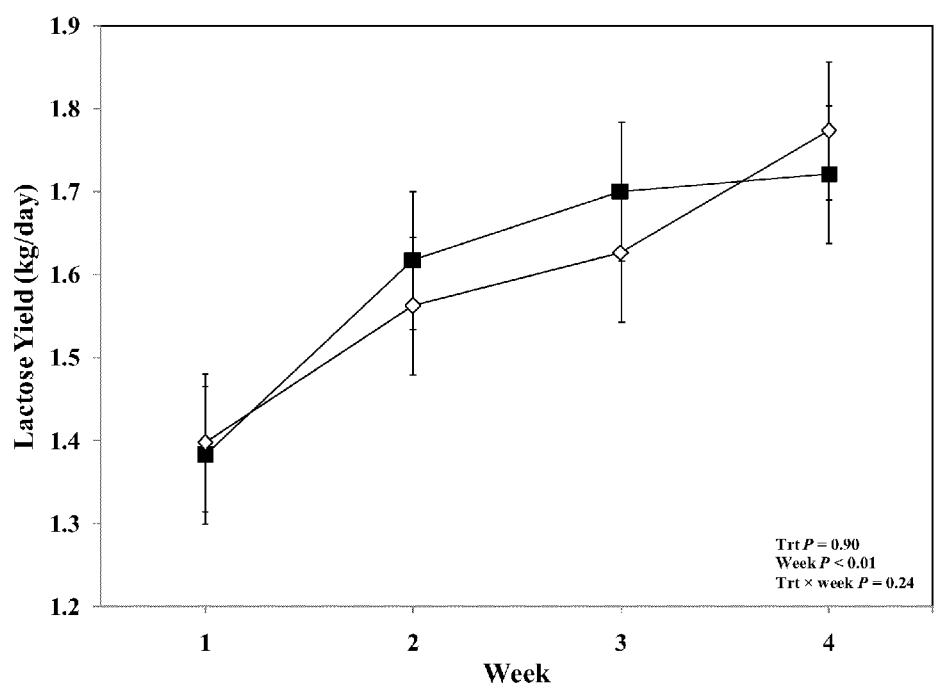
FIG. 15 is a graph depicting weekly variations of overall lactose yield in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 16:
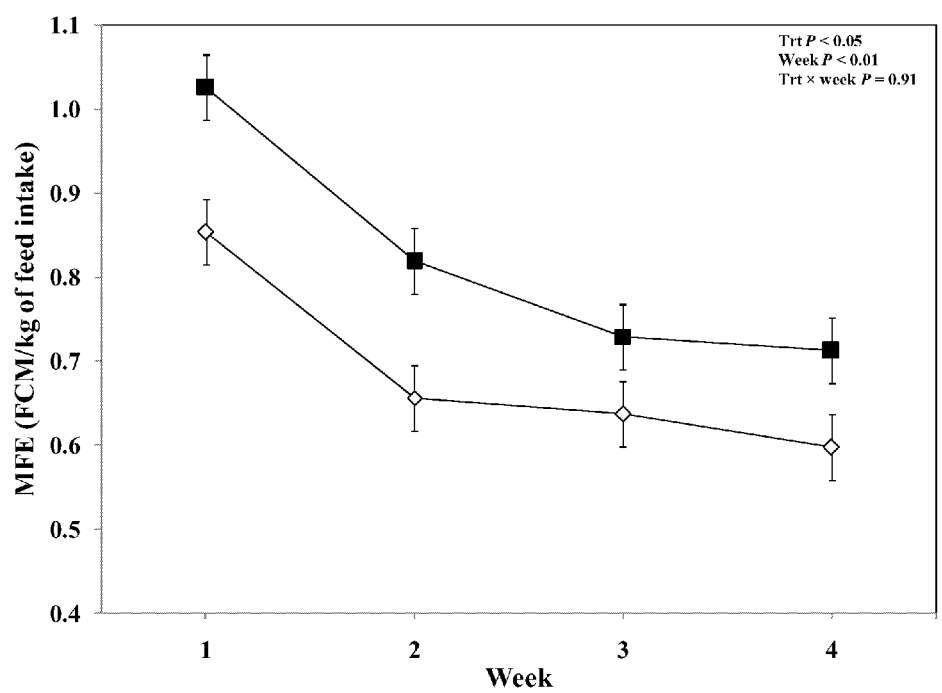
FIG. 16 is a graph depicting weekly variations of overall milk fat efficiency in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 17:
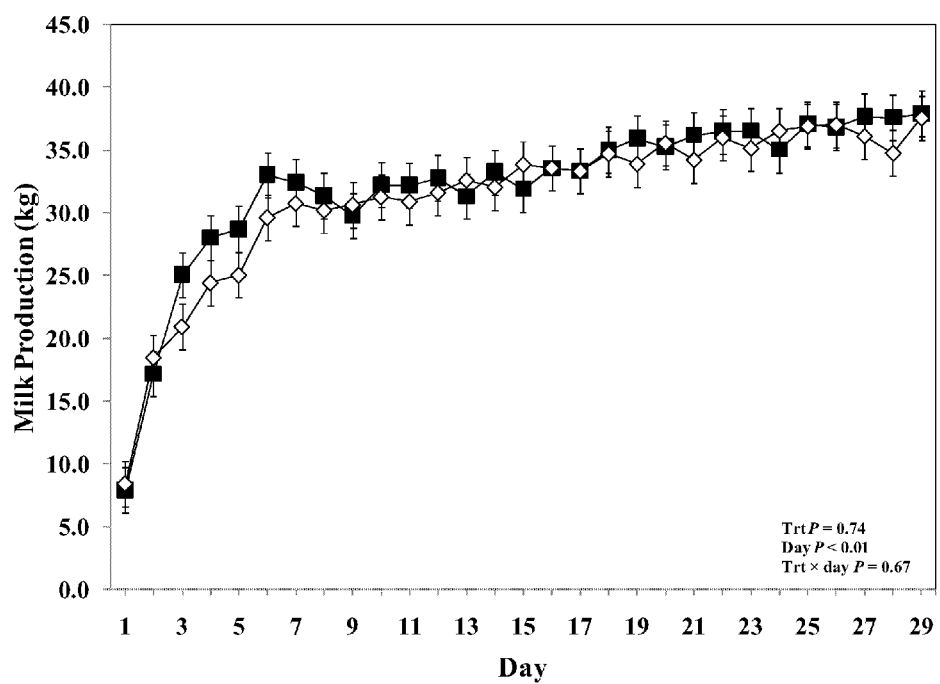
FIG. 17 is a graph depicting day-to-day variations of overall milk production in multiparous and primiparous lactating Holstein cows challenged with oral and nasal treatment of LPS-LTA (TRT; ■) or saline (CTR; ◊) (LSM±SEM; n=30; Trt=effect of treatment; Day=effect of sampling day, Trt×day=effect of treatment by sampling day).
Figure 18:
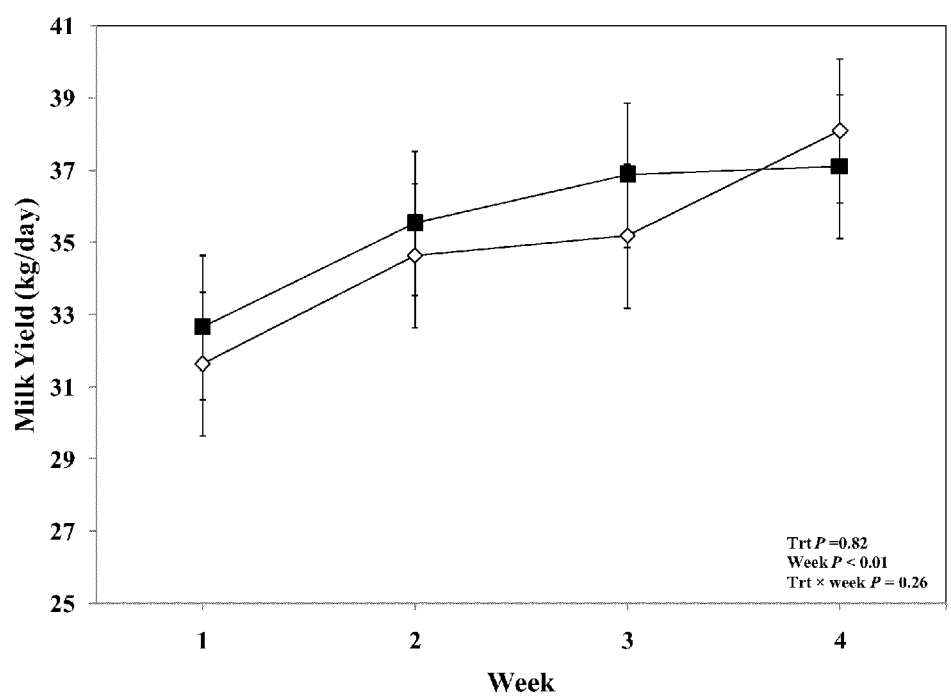
FIG. 18 is a graph depicting weekly variations of overall milk yield in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 19:
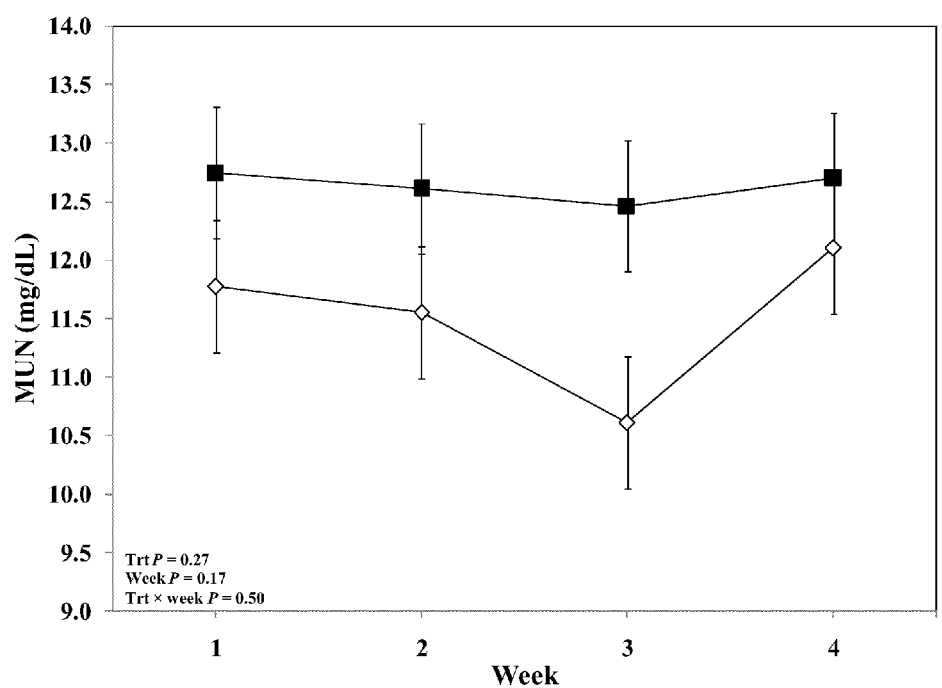
FIG. 19 is a graph depicting weekly variations of overall milk urea nitrogen in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 20:
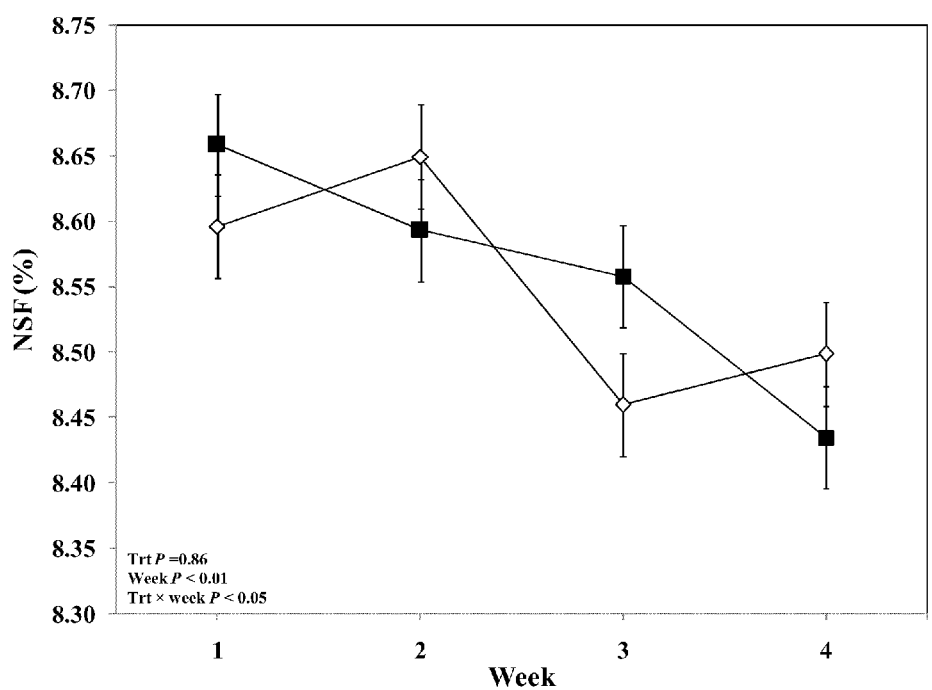
FIG. 20 is a graph depicting weekly variations of overall milk solid not fat in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 21:
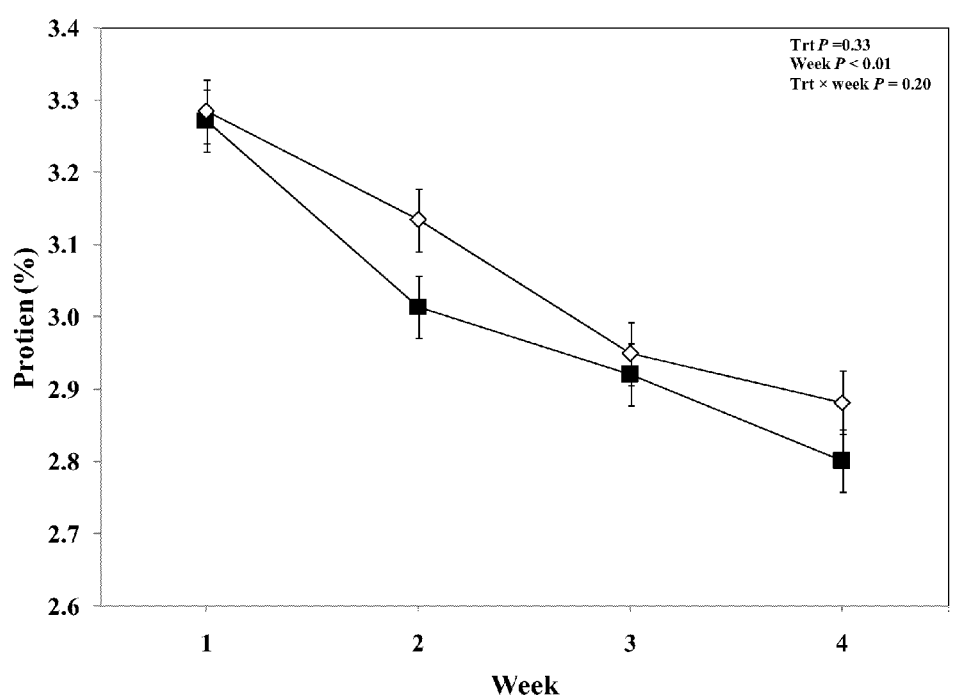
FIG. 21 is a graph depicting weekly variations of overall milk protein content in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 22:
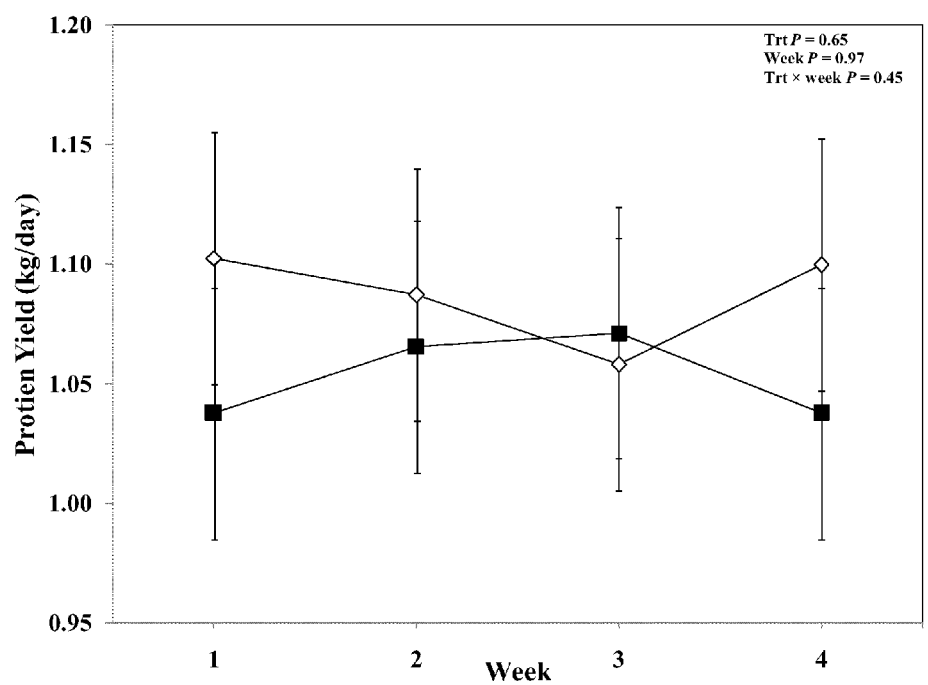
FIG. 22 is a graph depicting weekly variations of overall milk protein yield in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 23:
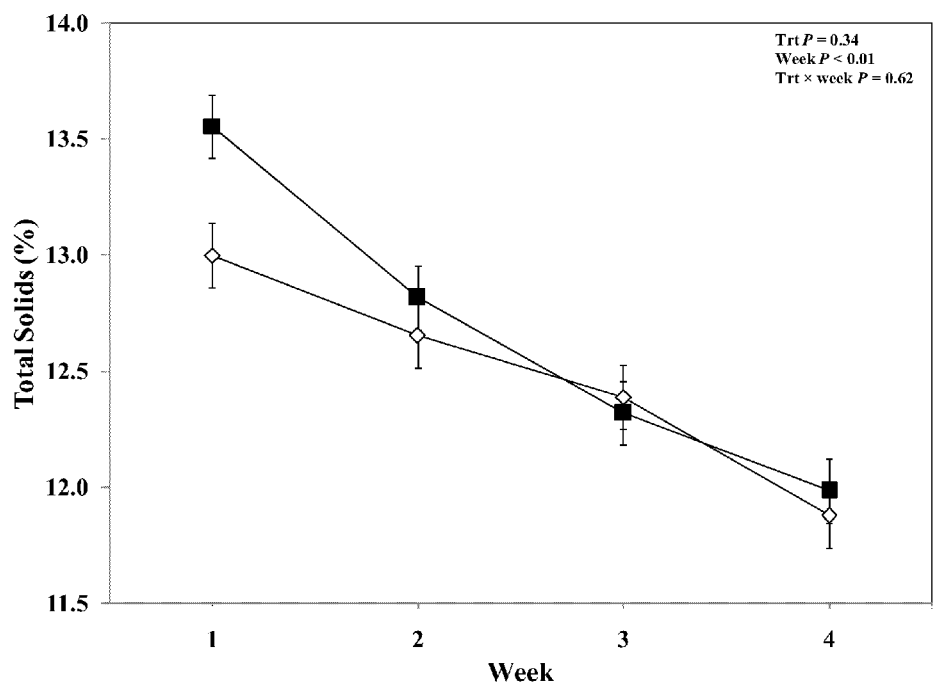
FIG. 23 is a graph depicting weekly variations of overall total solid contents in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 24:
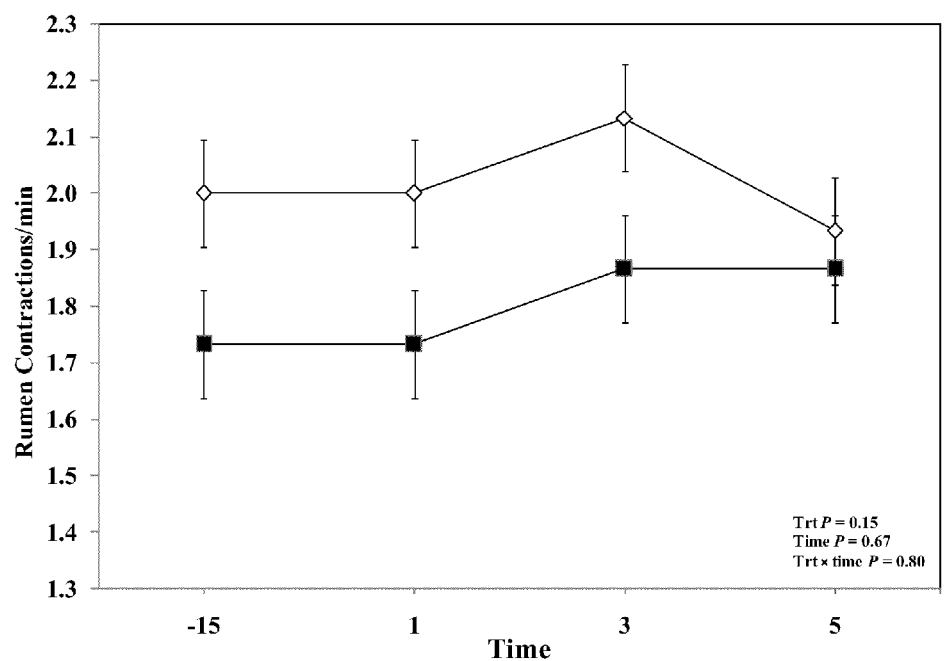
FIG. 24 is a graph depicting the effect of measurement time on diurnal variations of rumen contractions per minute in multiparous and primiparous lactating Holstein cows challenged with oral and nasal treatment of LPS-LTA (TRT; ■) or saline (CTR; ◊) (LSM±SEM; n=10; Trt=effect of treatment; Time=effect of time measured before and after treatment, Trt×time=effect of treatment by measurement time).
Figure 25:
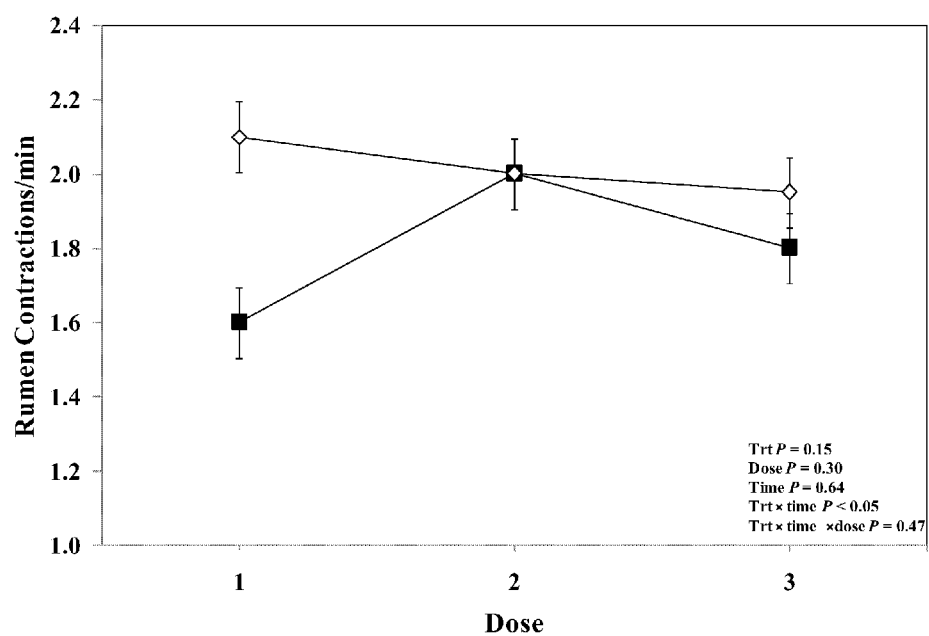
FIG. 25 is a graph depicting diurnal variations of rumen contractions per minute in multiparous and primiparous lactating Holstein cows challenged with three different doses of oral and nasal treatment of LPS-LTA (TRT; ■) or saline (CTR; ◊) (LSM±SEM; n=10; Trt=effect of treatment; Time=effect of time measured before and after treatment, Trt×time=effect of treatment by measurement time).
Figure 26:
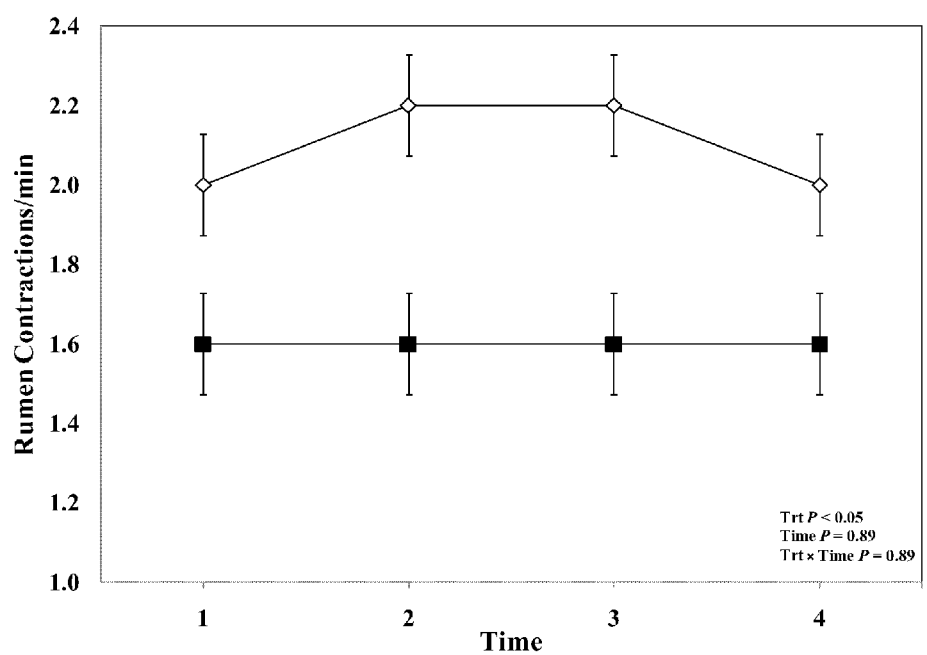
FIG. 26 is a graph depicting diurnal variations of rumen contractions per minute in multiparous and primiparous lactating Holstein cows challenged with first dose of oral and nasal treatment of LPS-LTA (TRT; ■) or saline (CTR; ◊) (LSM±SEM; n=10; Trt=effect of treatment; Time=effect of time measured before and after treatment, Trt×time=effect of treatment by measurement time).
Figure 27:
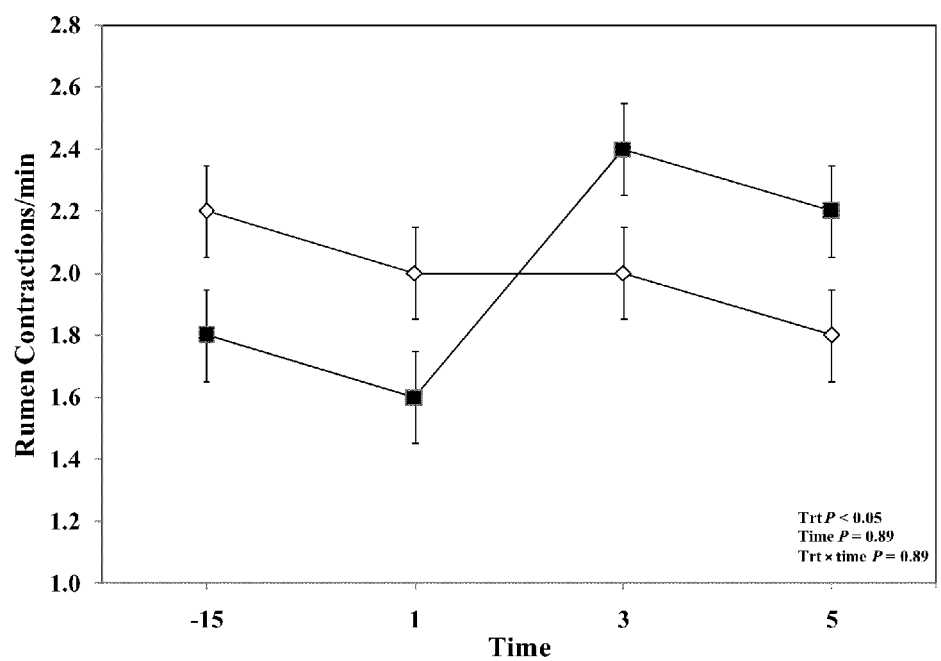
FIG. 27 is a graph depicting diurnal variations of rumen contractions per minute in multiparous and primiparous lactating Holstein cows challenged with second dose of oral and nasal treatment of LPS-LTA (TRT; ■) or saline (CTR; ◊)
Figure 28:
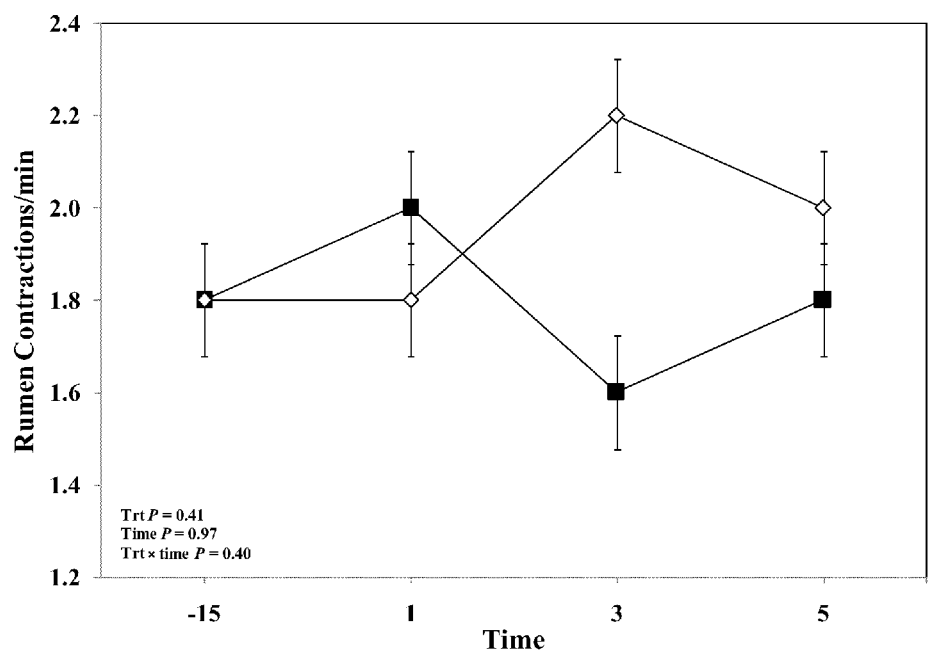
FIG. 28 is a graph depicting diurnal variations of rumen contractions per minute in multiparous and primiparous lactating Holstein cows challenged with third dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 29:
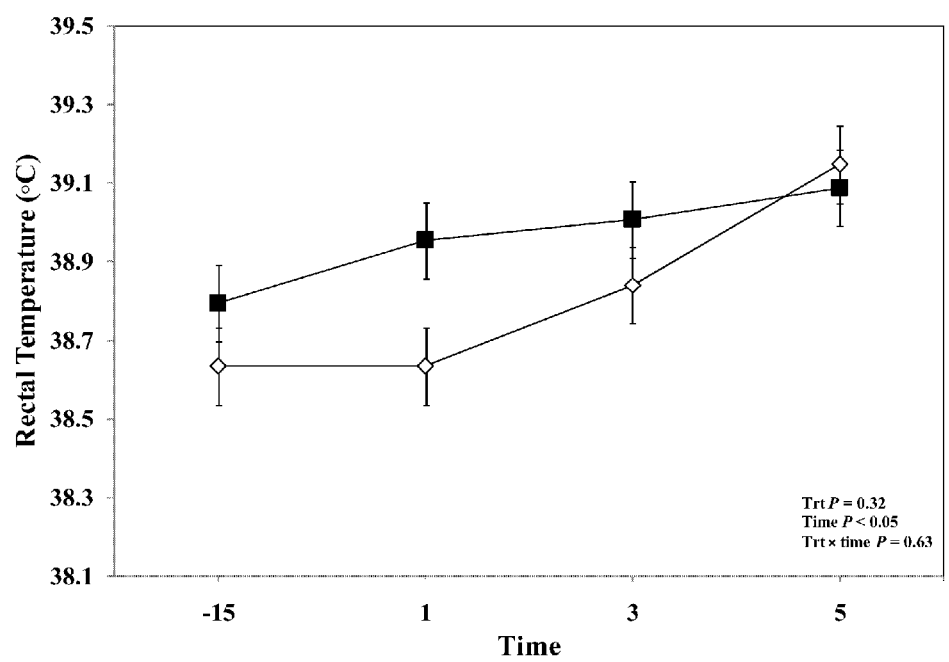
FIG. 29 is a graph depicting the effect of measurement time on diurnal variations of rectal temperature in multiparous and primiparous lactating Holstein cows challenged with oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 30:
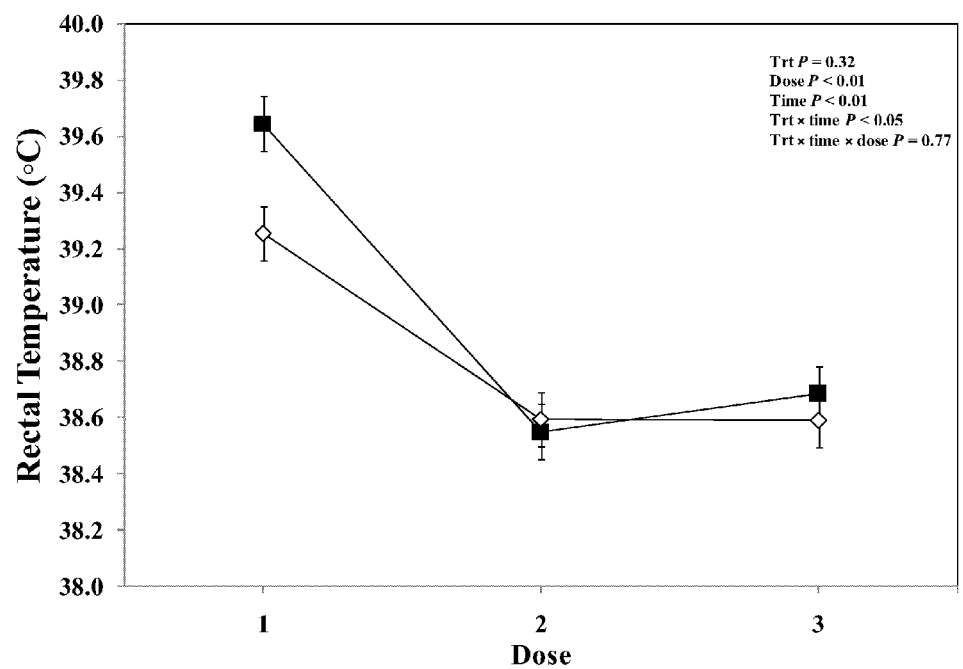
FIG. 30 is a graph depicting diurnal variations of rectal temperature in multiparous and primiparous lactating Holstein cows challenged with three different doses of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 31:
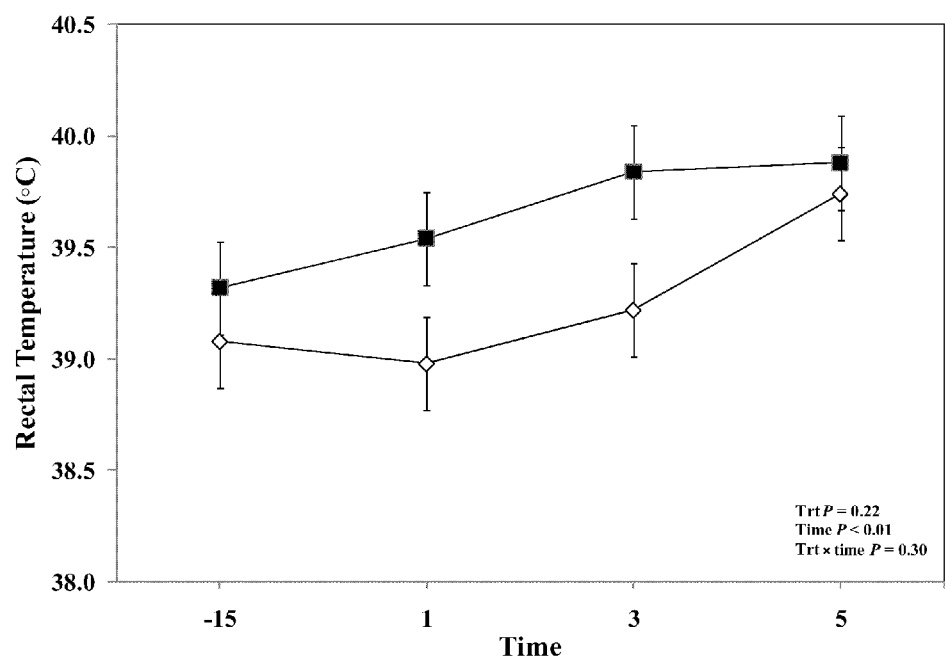
FIG. 31 is a graph depicting diurnal variations of rectal temperature in multiparous and primiparous lactating Holstein cows challenged with first dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 32:
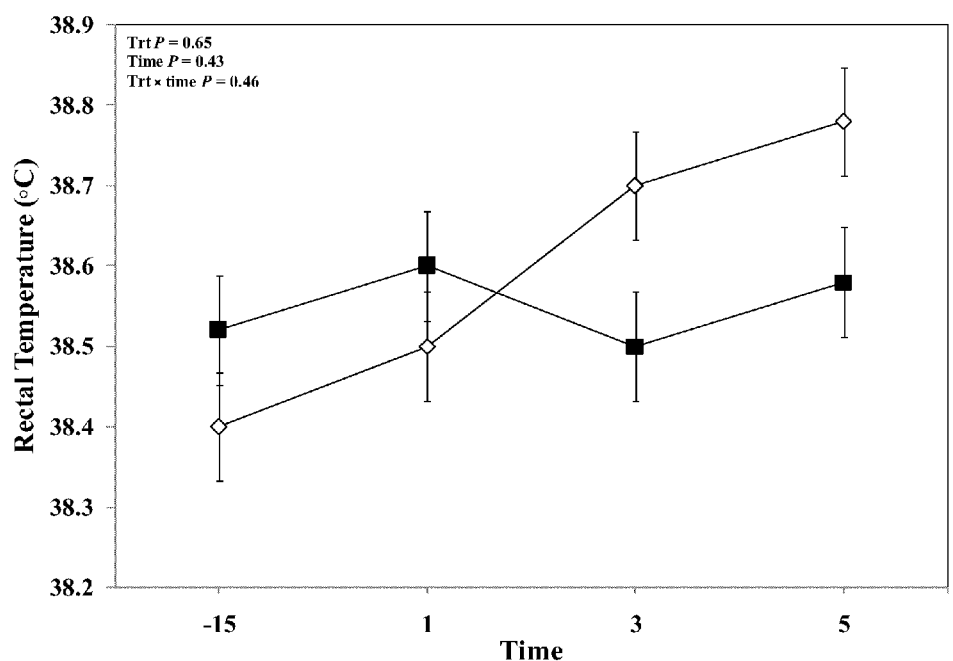
FIG. 32 is a graph depicting diurnal variations of rectal temperature in multiparous and primiparous lactating Holstein cows challenged with second dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 33:
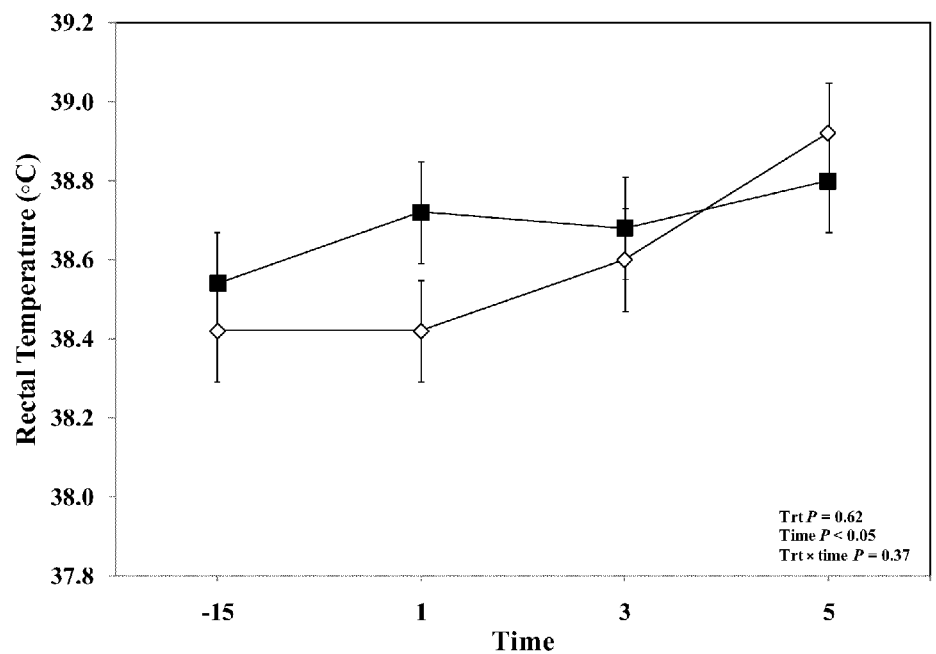
FIG. 33 is a graph depicting diurnal variations of rectal temperature in multiparous and primiparous lactating Holstein cows challenged with third dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 34:
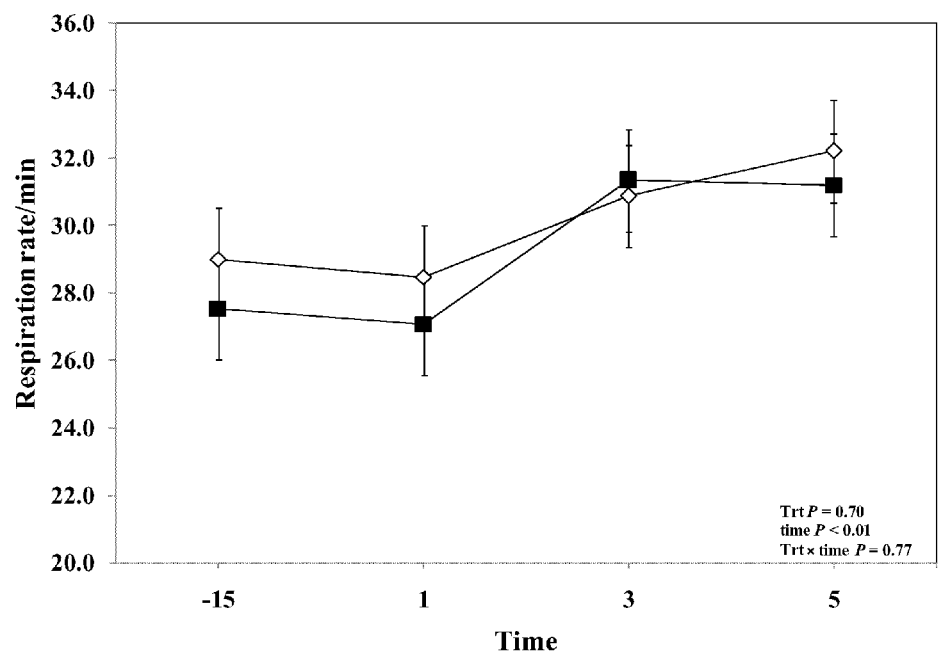
FIG. 34 is a graph depicting the effect of measurement time on diurnal variations of respiration rate per minute in multiparous and primiparous lactating Holstein cows challenged with oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 35:
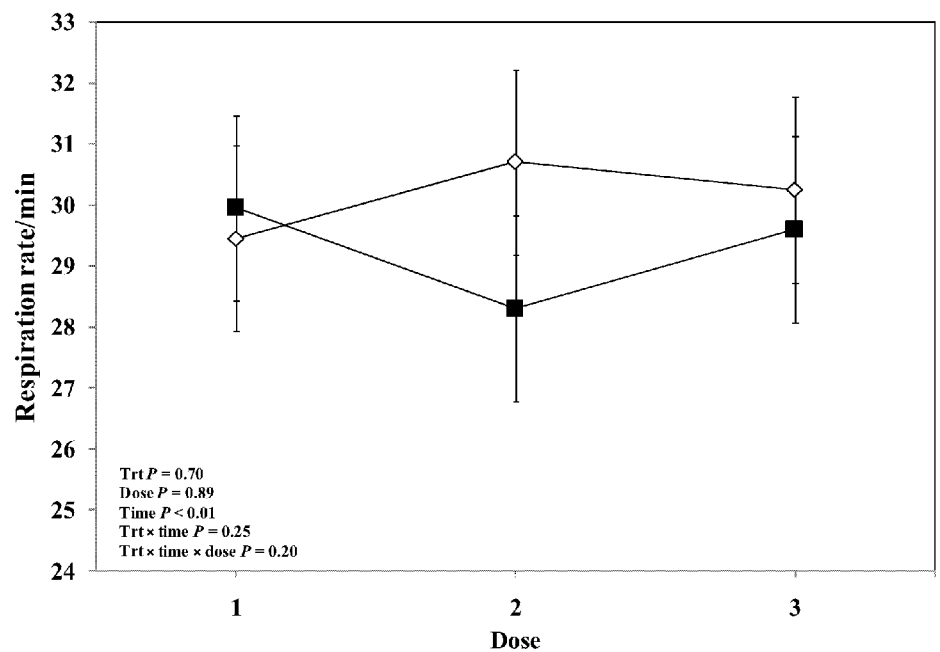
FIG. 35 is a graph depicting diurnal variations of respiration rate per minute in multiparous and primiparous lactating Holstein cows challenged with three different doses of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 36:
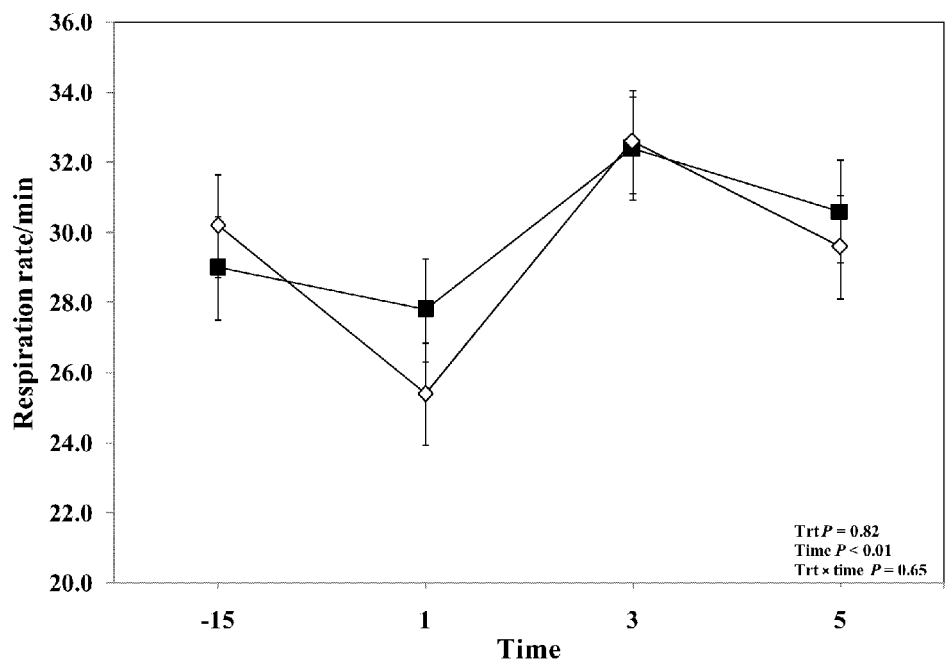
FIG. 36 is a graph depicting diurnal variations of respiration rate per minute in multiparous and primiparous lactating Holstein cows challenged with first dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 37:
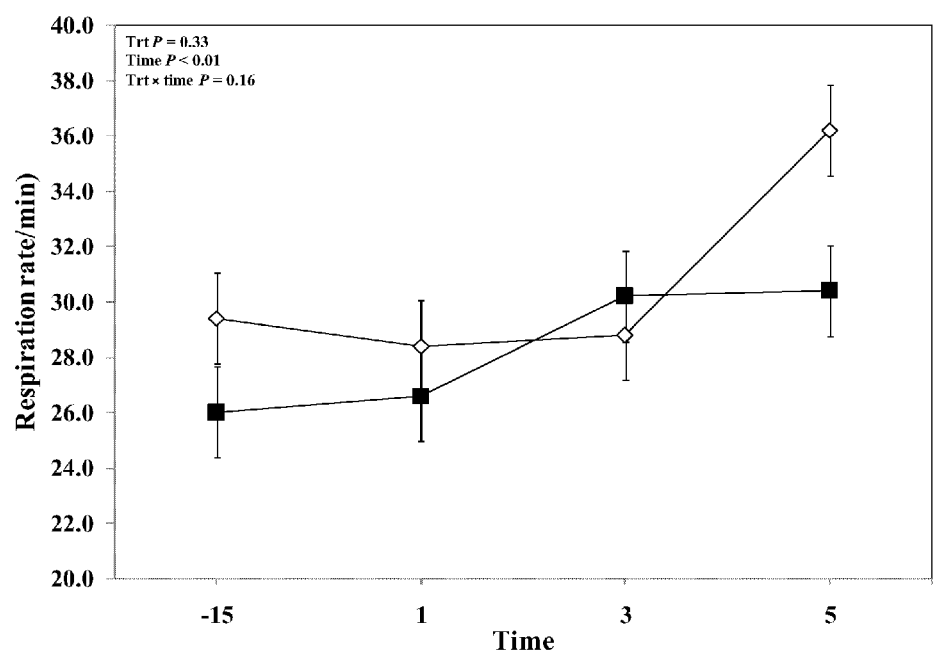
FIG. 37 is a graph depicting diurnal variations of respiration rate per minute in multiparous and primiparous lactating Holstein cows challenged with second dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).
Figure 38:
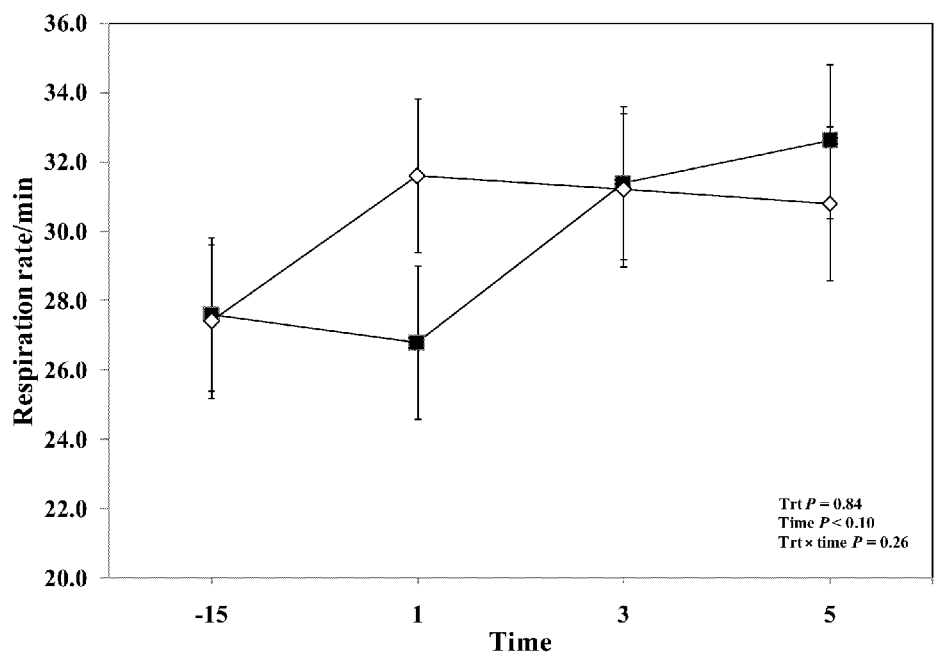
FIG. 38 is a graph depicting diurnal variations of respiration rate per minute in multiparous and primiparous lactating Holstein cows challenged with third dose of oral and nasal treatment of LPS-LTA (TRT; ■) or saline (CTR; ◇) (LSM±SEM; n=10; Trt=effect of treatment; Time=effect of time measured before and after treatment, Trt×time=effect of treatment by measurement time).

Interestingly, data indicated that the oral vaccination of cows with LPS and LTA increased their milk energy efficiency (see FIGS. 7 and 8), which was associated with a trend for greater feed intake in that group (see FIG. 13).

Figure 9:
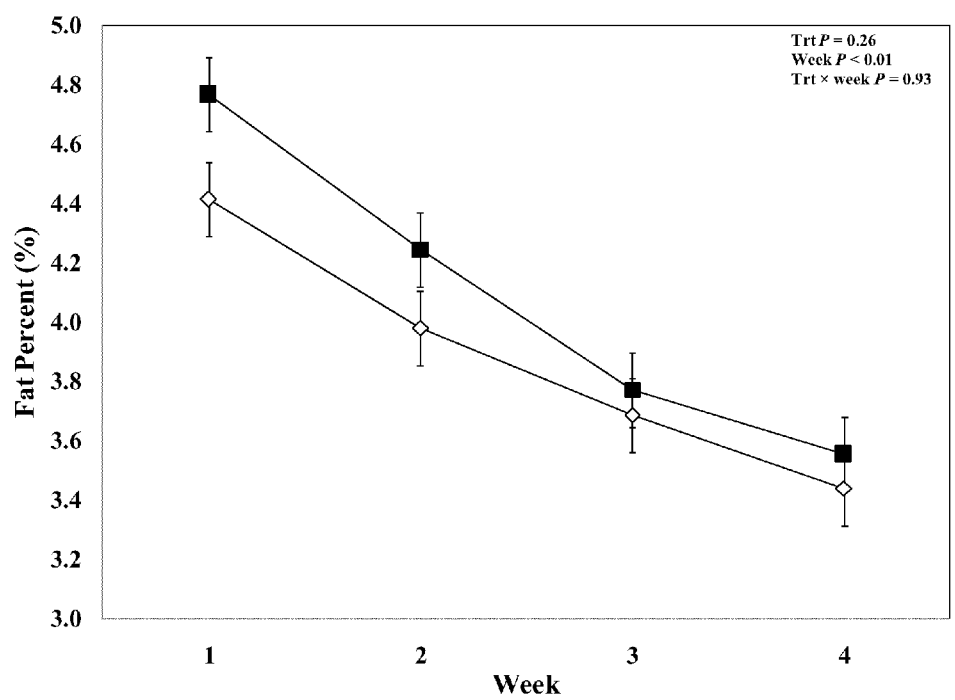
FIG. 9 is a graph depicting weekly variations of overall fat percent in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 10:
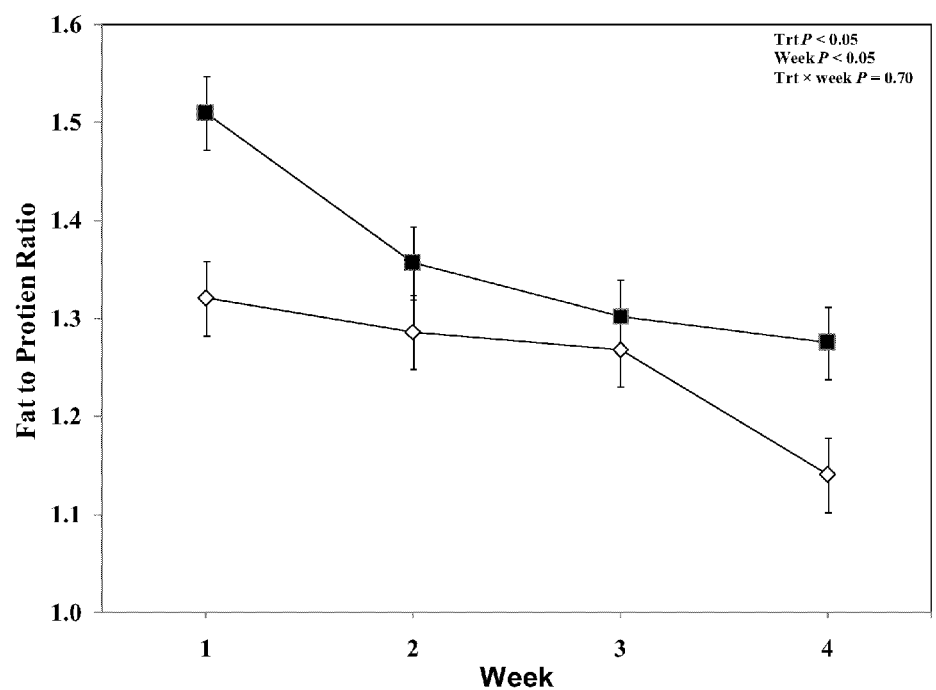
FIG. 10 is a graph depicting weekly variations of overall fat to protein ratio in multiparous and primiparous lactating Holstein cows challenged with oral and nasal treatment of LPS-LTA (TRT; ■) or saline (CTR; ◊) (LSM±SEM; n=30; Trt=effect of treatment; Week=effect of sampling week, Trt×Week=effect of treatment by sampling week).
Figure 11:
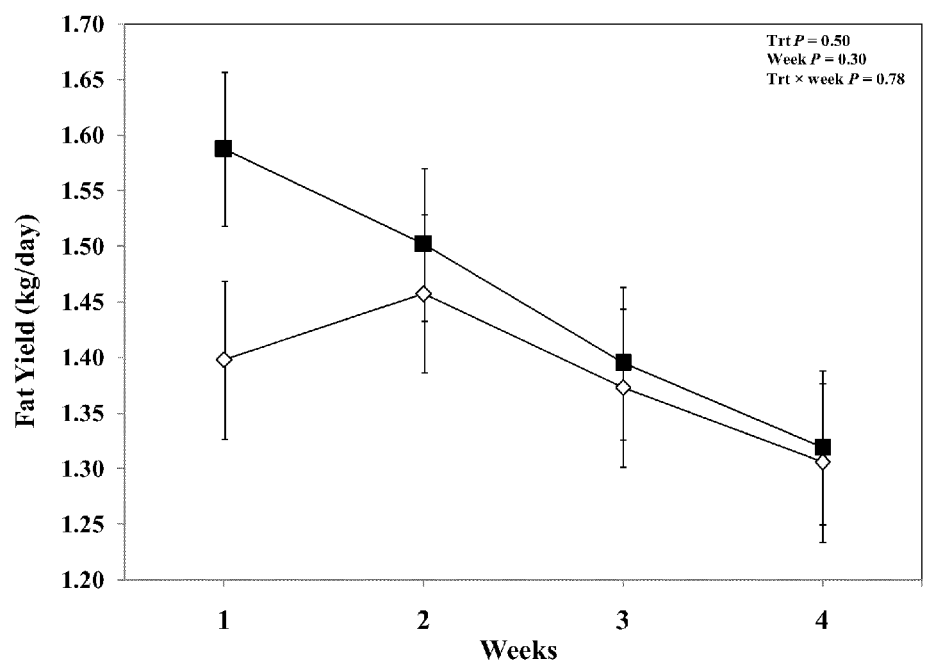
FIG. 11 is a graph depicting weekly variations of overall fat yield in multiparous and primiparous lactating Holstein cows challenged with oral and nasal treatment of LPS-LTA (TRT; ■) or saline (CTR; ◊) (LSM±SEM; n=29; Trt=effect of treatment; Week=effect of sampling week, Trt×Week=effect of treatment by sampling week).
Figure 12:
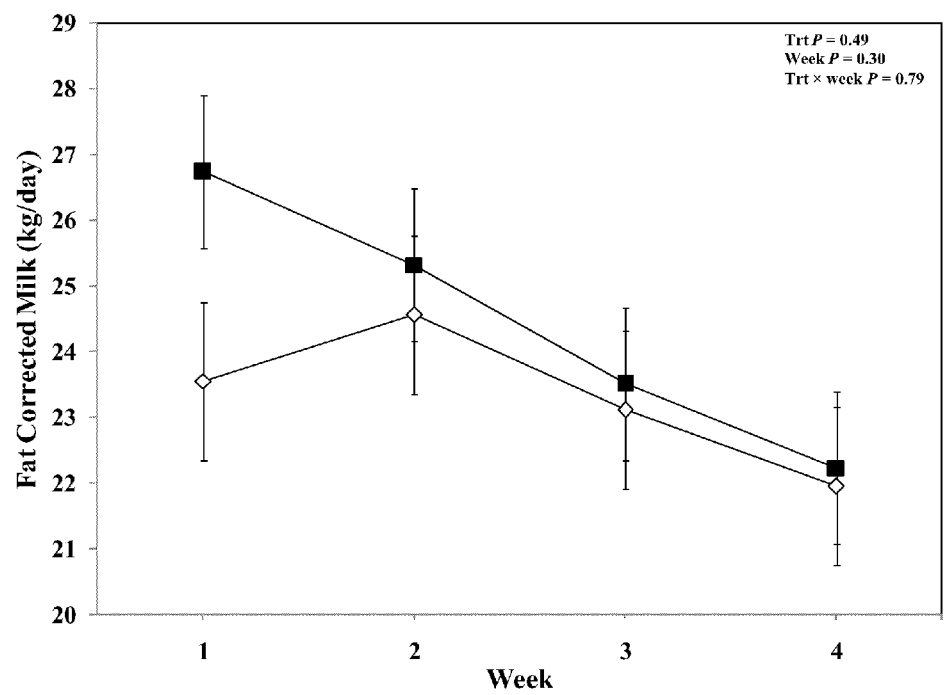
FIG. 12 is a graph depicting weekly variations of overall fat corrected milk in multiparous and primiparous lactating Holstein cows challenged with oral and nasal treatment of LPS-LTA (TRT; ■) or saline (CTR; ◊) (LSM±SEM; n=29; Trt=effect of treatment; Week=effect of sampling week, Trt×Week=effect of treatment by sampling week).

Furthermore, the analysis of milk data demonstrated a higher fat to protein ratio (see FIGS. 9 and 10), as well as greater milk fat efficiency for the treated cows (see FIGS. 11 and 12).

No effect of treatment was observed on other milk components as well as on the overall milk production (see FIGS. 14-23). Calf data indicated a tendency for lower calf diarrhoea score in the treatment group for both multiparous and primiparous cows compared to controls.

Clinical Results

Results of this study demonstrated that oral administration of LPS and LTA was associated with lower incidence of metritis, laminitis, retained placenta, and improved uterine horn fluctuation in the treated cows (see FIGS. 24-38). Furthermore, the severity of laminitis was lowered in treated multiparous cows, where it tended to be lower in the treatment group. Moreover, treated cows tended to require lower overall number of medications as well as have lower number of days with more than one disease versus control cows.

EXAMPLE 3

Preliminary LTA Dosage Study

This study aimed at establishing metabolic and clinical responses to increasing oral doses of LTA and the oral dose that will initiate clinical symptoms in dairy cows. Seven late lactating Holstein dairy cows of an average BW of 800±30 kg were randomly allocated to an oral administration of 2 mL saline solution containing one of the following LTA doses 20, 40, 70, 100, 120, 150, and 200 μg to each cow, respectively. Blood samples were collected from the tail vein at −15 min, 1, 3, and 5 h, whereas clinical responses were observed at −15 min, 1, 2, 3, 4, 5, and 6 h after the oral administration of each dose of LTA.

Blood data demonstrated that oral administration of LTA increased concentration of glucose in the plasma with the highest doses (150 and 200 μg) having the highest plasma glucose (P<0.01). Furthermore, plasma glucose linearly increased with time after oral administration of LTA (P<0.01). Interestingly, cows also showed greater concentrations of plasma cholesterol at the highest doses of 150 and 200 μg (P<0.01). Also, concentrations of non-esterified fatty acid in the plasma were found higher at 150 and 200 μg doses (P<0.01). No effect of any of the doses of LTA used was observed on the concentration of beta-hydroxybutyric acid in the plasma (P>0.05). On the other hand, clinical data indicated that oral LTA influenced rectal temperatures and respiration rates, although the variations were within the normal ranges ($P<0.01$ and $P<0.01$, respectively).

Interestingly, the highest doses of LTA (150 and 200 µg) lowered rumen contractions ($P<0.01$), whereas all other doses did not have an effect on this variable. Overall, oral administration of increasing doses of LTA modulated plasma patterns of selected metabolites and clinical responses of late lactating dairy cows. It was also determined that the clinical safe dose of oral LTA to be used in future experiments was 120 µg dose.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Unless defined otherwise, all technical and scientific terms used herein have the same meaning as commonly understood to one of ordinary skill in the art to which this invention belongs. As used in this specification and the appended claims, the singular forms "a", "an", and "the" include plural reference unless the context clearly dictates otherwise.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for treating a metabolic disorder in a cow, said method comprising administering to said cow a bacterial endotoxin and a lipoteichoic acid, separately, simultaneously or sequentially, wherein said metabolic disorder is metritis, laminitis, retained placenta or impaired uterine horn fluctuation.

2. The method according to claim 1, wherein said metabolic disorder is associated with parturition.

3. The method according to claim 1, comprising administering said endotoxin and said lipoteichoic acid to said cow from a time no more than four weeks prior to parturition to a time no more than four weeks after parturition.

4. The method according to claim 1, comprising administering said endotoxin in a dose of from 0.001 to 1 µg endotoxin/kg body weight of said cow.

5. The method according to claim 4, wherein said dose comprises about 0.01, about 0.05 or about 0.1 µg endotoxin/kg body weight of said cow.

6. The method according to claim 1, comprising administering said lipoteichoic acid in a dose of from 0.1 to 1000 µg lipoteichoic acid.

7. The method according to claim 6, wherein said acid dose comprises about 100, about 120 or about 250 µg lipoteichoic acid.

8. The method according to claim 1, wherein said cow is a dairy cow.

* * * * *